United States Patent [19]
Dawson et al.

[11] Patent Number: 5,932,213
[45] Date of Patent: *Aug. 3, 1999

[54] MODIFIED PLASMIN PRECURSORS WITH RESISTANCE TO INHIBITORS OF PLASMIN

[75] Inventors: Keith Martyn Dawson; Richard James Gilbert, both of Cowley, United Kingdom

[73] Assignee: British Biotech Pharmaceuticals, Ltd., Oxford, United Kingdom

[ * ] Notice: This patent is subject to a terminal disclaimer.

[21] Appl. No.: 08/889,078

[22] Filed: Jul. 7, 1997

Related U.S. Application Data

[63] Continuation of application No. 08/379,621, Feb. 3, 1995

[60] Provisional application No. PCT/GB93/01632, Aug. 3, 1993, Pat. No. 5,645,833.

[30] Foreign Application Priority Data

Aug. 4, 1992 [GB] United Kingdom ................... 9216558

[51] Int. Cl.$^6$ .............................. C12N 9/68; C12N 15/55; A61K 38/48
[52] U.S. Cl. ........................ 424/94.64; 435/217; 536/23.2
[58] Field of Search ........................ 424/94.64; 435/217, 435/320.1; 536/23.2

[56] References Cited

FOREIGN PATENT DOCUMENTS

| | | |
|---|---|---|
| 0381331 | 8/1990 | European Pat. Off. . |
| WO9010649 | 9/1990 | WIPO . |
| WO9109118 | 6/1991 | WIPO . |
| WO9206203 | 4/1992 | WIPO . |

*Primary Examiner*—Dian C. Jacobson
*Attorney, Agent, or Firm*—Hale and Dorr LLP

[57] ABSTRACT

Plasmin precursors are modified so that they exhibit resistance to inhibitors of plasmin. These modified plasmin precursors have fibrinolytic, thrombolytic or antithrombotic properties, which are useful in the treatment of blood clotting diseases or conditions.

7 Claims, 18 Drawing Sheets

```
                           1                                              50
Complement Factor B    WEHRKGTDYH KQPWQAKISV IRPSKGH..E SCMGAVVSEY FVLTAAHCF.
Complement C2          GVGNMSANAS DQERTPWHVT IKP.KSQ..E TCRGALISDQ WVLTAAHCF.
Medullasin             IVGGRRARPH AWPFMVSLQL R...GG...H FCGATLIAPN FVMSAAHCV.
Myeloblastin           .......... ....MASLQM RGNPGS...H FCGGTLIHPS FVLTAAHCL.
Complement C1S         IIGGSDADIK NFPWQVFF.. ...D.NP... WAGGALINEY WVLTAAHVV.
Complement C1R         IIGGQKAKMG NFPWQVFT.. ...NIHG... RGGGALLGDR WILTAAHTL.
Factor X               IVGGQECKDG ECPWQALLI. NEENEG.... FCGGTILSEF YILTAAHCL.
Factor IX              VVGGEDAKPG QFPWQVVL.. NGKVDA.... FCGGSIVNEK WIVTAAHCV.
Factor VII             IVGGKVCPKG ECPWQVLLL. VNGAQ..... LCGGTLINTI WVVSAAHCF.
Protein C              LIDGKMTRRG DSPWQVVLL. DSKKKL.... ACGAVLIHPS WVLTAAHCM.
Thrombin               IVEGSDAEIG MSPWQVMLFR KSPQEL.... LCGASLISDR WVLTAAHCLL
u-PA                   IIGGEFTTIE NQPWFAAIYR RH.RGGSVTY VCGGSLMSPC WVISATHCF.
t-PA                   IKGGLFADIA SHPWQAAIFA KHRRSPGERF LCGGILISSC WILSAAHCF.
Factor XII             VVGGLVALRG AHPYIAALYW GHS....... FCAGSLIAPC WVLTAAHCL.
Apolipoprotein A       IVGGCVAHPH SWPWQVSL.R .TRFGK...H FCGGTLISPE WVLTAAHCL.
Plasmin                VVGGCVAHPH SWPWQVSL.R .TRFGM...H FCGGTLISPE WVLTAAHCL.
Hepsin                 IVGGRDTSLG RWPWQVSL.R .YD.GA...H LCGGSLLSGD WVLTAAHCF.
Elastase IIIa          VVHGEDAVPY SWPWQVSL.Q .YEKSGSFYH TCGGSLIAPD WVVTAGHCI.
Elastase IIIb          VVNGEDAVPY SWPWQVSL.Q .YEKSGSFYH TCGGSLIAPD WVVTAGHCI.
```

```
                          1                                                      50
Elastase IIa         VVGGEEARPN SWPWQVSL.Q .YSSNGKWYH TCGGSLIANS WVLTAAHCI.
Elastase IIb         MLGGEEARPN SWPWQVSL.Q .YSSNGQWYH TCGGSLIANS WVLTAAHCI.
Chymotrypsin B       IVNGEDAVPG SWPWQVSL.Q .DKTG...FH FCGGSLISED WVVTAAHCG.
Alpha Tryptase       IVGGQEAPRS KWPWQVSL.R .VR.DRYWMH FCGGSLIHPQ WVLTAAHCL.
Beta Tryptase        IVGGQEAPRS KWPWQVSL.R .VH.GPYWMH FCGGSLIHPQ WVLTAAHCV.
Factor XI            IVGGTASVRG EWPWQVTL.H .TT.SPTQRH LCGGSIIGNQ WILTAAHCF.
Plasma Kallikrein    IVGGTNSSWG EWPWQVSL.Q .VK.LTAQRH LCGGSLIGHQ WVLTAAHCF.
Acrosin              IVGGKAAQHG AWPWMVSL.Q IFRYNSHRYH TCGGSLLNSR WVLTAAHCF.
Trypsin I            IVGGYNCEEN SVPYQVSL.. ..NS.G..YH FCGGSLINEQ WVVSAGHCY.
Trypsin II           IVGGYICEEN SVPYQVSL.. ..NS.G..YH FCGGSLISEQ WVVSAGHCY.
Trypsin III          IVGGYTCEEN SLPYQVSL.. ..NS.G..SH FCGGSLISEQ WVVSAAHCY.
Tissue Kallikrein 2  IVGGWECEKH SQPWQVAV.. ..YSHG..WA HCGGVLVHPQ WVLTAAHCL.
PSA                  IVGGWECEKH SQPWQVLV.. ..ASRG..RA VCGGVLVHPQ WVLTAAHCI.
Tissue Kallikrein 1  IVGGWECEQH SQPWQAAL.. ..YHFS..TF QCGGILVHRQ WVLTAAHCI.
Granzyme B           IIGGHEAKPH SRPYMAYL.M IWDQKS..LK RCGGFLIQDD FVLTAAHCW.
T-cell Granzyme      IIGGHEAKPH SRPYMAFV.Q FLQEKS..RK RCGGILVRKD FVLTAAHCQ.
Cathepsin G          IIGGRESRPH SRPYMAYL.Q IQSPAG..QS RCGGFLVRED FVLTAAHCW.
Complement Factor D  ILGGREAEAH ARPYMASV.Q L..NG..AH LCGGVLVAEQ WVLSAAHCL.
Granzyme A           IIGGNEVTPH SRPYMVLL.S L..DR..KT ICAGALIAKD WVLTAAHC..
Complement Factor I  IVGGKRAQLG DLPWQVAIKD ASGIT..... .CGGIYIGGC WILTAAHCL.
```

FIG. 1C

```
                         51                                                          100
Complement Factor B   ...TVDDKEH SI.KVSVGGE K....RDLEI EVLLFHPNYN INGKKEAGIP
      Complement C2   ...R.DGNDH SLWRVNVGDP KSQWGKELLI EKAVISPGFD VFAKKNQGIL
         Medullasin   .....ANVNV RAVRVVLGAH NLSRREPTRQ VFAVQRIFEN GYDPVNLL..
        Myeloblastin   .....RDIPQ RLVNVVLGAH NVRTQEPTQQ HFSVAQVFLN NYDAENKL..
      Complement C1s   .......EGN REPTMYVGST SVQTSRLAKS KMLTPEHVFI HPGWKLLEVP
      Complement C1R   YPKEHEAQSN ASLDVFLGHT NVEE..LMKL GNHPIRRVSV HPDYR....Q
            Factor X   ....YQAK.. .RFKVRVGDR NTEQEEGG.E AVHEVEVVIK HNRF......
           Factor IX   ....ETGV.. .KITVVAGEH NIEETEHT.E QKRNVIRIIP HHNYNA....
          Factor VII   ....DKIKNW RNLIAVLGEH DLSEHDGD.E QSRRVAQVII PSTYVP....
           Protein C   ....DESK.. .KLLVRLGEY DLRRWEKW.E LDLDIKEVFV HPNY......
            Thrombin   YPPWDKNFTE NDLLVRIGKH SRTRYERNIE KISMLEKIYI HPRYNW....
                u-PA   .IDYPKKE.. .DYIVYLGRS RLNSNTQGEM KF..........EVENLILH
                t-PA   .QERFPPH.. .HLTVILGRT YRVVPGEEEQ KF..........EVEKYIVH
          Factor XII   .QDRPAPE.. .DLTVVLGQE RRNHSCEPCQ TL..........AVRSYRLH
      Apolipoprotein A   .K..KSSRP. SSYKVILGAH QEV...NLES HV.....QE...IEVSRLFL
             Plasmin   .E..KSPRP. SSYKVILGAH QEV...NLEP HV.....QE...IEVSRLFL
              Hepsin   .P..ERNRVL SRWRVFAGAV AQASPHGLQL GV.....QA...WYHGGYL
        Elastase IIIa   .S...RD.... LTYQVVLGEY NLAVKEGPEQ VI.....PI...NSEELFVH
        Elastase IIIb   .S...SS.... RTYQVVLGEY DRAVKEGPEQ VI.....PI...NSGDLFVH
         Elastase IIa   .S...SS.... RTYRVGLGRH NLYVAESGSL AV.....SV....SKIVVH
```

```
                       51                                                           100
Elastase IIb       .S..SS..... RIYRVMLGQH NLYVAESGSL AV......SV. ....SKIVVH
Chymotrypsin B     .V..RT..... SDV.VVAGEF DQGSDEENIQ VL......KI. ....AKVFKN
Alpha Tryptase     .G..PDVKDL ATLRVN.SGT HLYYQDQLLP VS......RI. ..MVHPQFYI
Beta Tryptase      .G..PDVKDL AALRVQLREQ HLYYQDQLLP VS......RI. ..IVHPQFYT
Factor XI          .YGVESPKIL RVYSGILNQS EIKEDTSFFG VQ......EI. ..IIHDQYKM
Plasma Kallikrein  .DGLPLQDVW RIYSGILNLS DITKDTPFSQ IK......EI. ..IIHQNYKV
Acrosin            .VGKNNVHD. ..WRLVFGAK EITYGNNKPV KA......PLQ ERYVEKIIIH
Trypsin I          ......KSRI. ...QVRLGEH NIEVLEGNEQ F.INAAKIIR HPQYDRKTLN
Trypsin II         ......KSRI. ...QVRLGEH NIEVLEGNEQ F.INAAKIIR HPKYNSRTLD
Trypsin III        ......KTRI. ...QVRLGEH NIKVLEGNEQ F.INAAKIIR HPKYNRDTLD
Tissue Kallikrein 2 .....KKNS. ...QVWLGRH NLFEPEDTGQ R.VPVSHSFP HPLYNMSLLK
PSA                ......RNKS. ...VILLGRH SLFHPEDTGQ V.FQVSHSFP HPLYDMSLLK
Tissue Kallikrein 1 .....SDNY. ...QLWLGRH NLFDDENTAQ F.VHVSESFP HPGFNMSLLE
Granzyme B         ......GSSIN ....VTLGAH NIKEQEPTQQ F.IPVKRPIP HPAYNPKNFS
T-cell Granzyme    ......GSSIN ....VTLGAH NIKEQERTQQ F.IPVKRPIP HPAYNPKNFS
Cathepsin G        ......GSNIN ....VTLGAH NIQRRENTQQ H.ITARRAIR HPQYNQRTIQ
Complement Factor D ....EDAAD GKVQVLLGAT HLPQPEPXXX ITIEVLRAVP HPDSQPDTID
Granzyme A         ......NLN KRSQVILGAH SITREEPTKQ IML.VKKEFP YPCYDPATRE
Complement Factor I ......RASKT HRYQIWTTVV DWIHPDLKRI VIEYVDRIIF HENYNA....
```

FIG. 1D

|  | 101 |  |  | 150 |
|---|---|---|---|---|
| Complement Factor B | EFY........ | DYDVALIKL. | ....KNKLKY | GQTIRPICLP CTEGTTRALR |
| Complement C2 | EFY........ | GDDIALLKL. | ....AQKVKM | STHARPICLP CTMEANLALR |
| Medullasin | ........... | .NDIVILQL. | ....NGSATI | NANVQVAQLP AQGR....RL |
| Myeloblastin | ........... | .NDILLIQL. | ....SSPANL | SASVTSVQLP QQDQ....PV |
| Complement C1S | E....GRTNF | DNDIALVRL. | ....KDPVKM | GPTVSPICLP GTSSDYNLMD |
| Complement C1R | D....ESYNF | EGDIALLEL. | ....ENSVTL | GPNLLPICLP DNDTFYDL.. |
| Factor X | .....TKETY | DFDIAVLRL. | ....KTPITF | RMNVAPACLP ERDWAESTL. |
| Factor IX | .....AINKY | NHDIALLEL. | ....DEPLVL | NSYVTPICIA DKEYTN.IF. |
| Factor VII | ......G..TT | NHDIALLRL. | ....HQPVVL | TDHVVPLCLP ERTFSERTL. |
| Protein C | ......SKSTT | DNDIALLHL. | ....AQPATL | SQTIVPICLP DSGLAERELN |
| Thrombin | ......RENL | DRDIALMKL. | ....KKPVAF | SDYIHPVCLP DRETAASLLQ |
| u-PA | KDYSADTLAH | HNDIALLKIR | SK.EGRCAQP | SRTIQTICLP SMY..NDPQF |
| t-PA | KEFDDDT..Y | DNDIALLQLK | SD.SSRCAQE | SSVVRTVCLP P....ADLQL |
| Factor XII | EAFS..PVSY | QHDLALLRLQ | EDADGSCALL | SPYVQPVCLP SGA..ARP.. |
| Apolipoprotein A | .......EPT | QADIALLKL. | ...SRPAV.I | TDKVMPACLP SPD..YMVT. |
| Plasmin | .......EPT | RKDIALLKL. | ...SSPAV.I | TDKVIPACLP SPN..YVVA. |
| Hepsin | PFRDPNSEEN | SNDIALVHL. | ...SSPLP.L | TEYIQPVCLP AAG..QALV. |
| Elastase IIIa | PLWNRSCVAC | GNDIALIKL. | ...SRSAQ.L | GDAVQLASLP PAG..DILP. |
| Elastase IIIb | PLWNRSCVAC | GNDIALIKL. | ...SRSAQ.L | GDAVQLASLP PAG..DILP. |
| Elastase IIa | KDWNSNQISK | GNDIALLKL. | ...ANPVS.L | TDKIQLACLP PAG..TILP. |

FIG.1E

```
                        101                                                          150
Elastase IIb            KDWNSNQVSK GNDIALLKL. ...ANPVS.L TDKIQLACLP PAG..TILP.
Chymotrypsin B          PKF..SILTV NNDITLLKL. ...ATPAR.F SQTVSAVCLP SAD..DDFP.
Alpha Tryptase          .......IQT GADIALLEL. ...EEPVN.I SSRVHTVMLP PAS..ETFP.
Beta Tryptase           .......AQI GADIALLEL. ...EEPVK.V SSHVHTVTLP PAS..ETFP.
Factor XI               ........AES GYDIALLKL. ...ETTVN.Y TDSQRPICLP SKG..DRNV.
Plasma Kallikrein       ........SEG NHDIALIKL. ...QAPLN.Y TEFQKPICLP SKG..DTST.
Acrosin                 EKYNS..ATE GNDIALVEI. ...TPPIS.C GRFIGPGCLP HFK..AGLP.
Trypsin I               N......... ..DIMLIKL. ...SSRA.VI NARVSTISLP TAP..PAT..
Trypsin II              N......... ..DILLIKL. ...SSPA.VI NSRVSAISLP TAP..PAA..
Trypsin III             N......... ..DIMLIKL. ...SSPA.VI NARVSTISLP TAP..PAA..
Tissue Kallikrein 2     HQSLRPDEDS SHDLMLLRL. ...SEPAK.I TDVVKVLGLP TQE..PAL..
PSA                     NRFLRPGDDS SHDLMLLRL. ...SEPAE.L TDAVKVMDLP TQE..PAL..
Tissue Kallikrein 1     NHTRQADEDY SHDLMLLRL. ...TEPADTI TDAVKVVELP TQE..PEV..
Granzyme B              N......... ..DIMLIQL. ...ERKAK.R TRAVQPLRLP SNK..AQVK.
T-cell Granzyme         N......... ..DIMLIQL. ...ERKAK.W TTAVRPLRLP SSK..AQVK.
Cathepsin G             N......... ..DIMLIQL. ...SRRVR.R NRNVNPVALP RAQ..EGLR.
Complement Factor D     H......... ..DLLLLQL. ...SEKAT.L GPAVRPLPWQ RVD..RDVA.
Granzyme A              G......... ..DLKLLQL. ...TEKAK.I NKYVTILHLP KKG..DDVK.
Complement Factor I     .......GTY QNDIALIEMK KDGNKKDCEL ......PRSIP ACVPWSPYLF
```

|  | 151 | | | | 200 |
|---|---|---|---|---|---|
| Complement Factor B | LPPTTCQQQ | KEELLPAQDI | KALFVSEEEK | KLTRKEVYIK | NGDKKGSC.E |
| Complement C2 | RPQGSTCRDH | ENELLNKQSV | PAHFVALNGS | KL...NINLK | MGVEWTSCAE |
| Medullasin | GNGVQCLAMG | WGLL...... | GRNRGIASVL | QELNVTV... | ..VT...... |
| Myeloblastin | PHGTQCLAMG | WGRV...... | GAHDPPAQVL | QELNVTV... | ..VT...... |
| Complement C1S | GDL..GLISG | WGRTEK.... | ...RDRAVRL | KAARLPV... | ..APLRKCKE |
| Complement C1R | GLM..GYVSG | FGVMEE.... | ...KI.AHDL | RFVRLPV... | ..ANPQACEN |
| Factor X | MTQKTGIVSG | FGRTHE.KGR | QS.....TRL | KMLEVPY... | ..VDRNSCKL |
| Factor IX | LKFGSGYVSG | WGRVFH.KGR | SA.....LVL | QYLRVPL... | ..VDRATCLR |
| Factor VII | AFVRFSLVSG | WGQLLD.RGA | TA.....LEL | MVLNVPR... | ..LMTQDCLQ |
| Protein C | QAGQETLVTG | WGYHSS.REK | EAKRNRTFVL | NFIKIPV... | ..VPHNECSE |
| Thrombin | AGYK.GRVTG | WGNLKETWTA | NVGKGQPSVL | QVVNLPI... | ..VERPVCKD |
| u-PA | G...TSCEITG | FGKENS.... | TDYLYPEQ.L | KMTVVKL... | ..ISHRECQQ |
| t-PA | PDWTECELSG | YGKHEA.... | LSPFYSER.L | KEAHVRL... | ..YPSSRCTS |
| Factor XII | SETTLCQVAG | WGHQFE.... | GAEEYASF.L | QEAQVPF... | ..LSLERCSA |
| Apolipoprotein A | ARTE.CYITG | WGETQG.... | TFG..TG.LL | KEAQLLV... | ..IENEVCNH |
| Plasmin | DRTE.CFITG | WGETQG.... | TFG..AG.LL | KEAQLPV... | ..IENKVCNR |
| Hepsin | DGKI.CTVTG | WGNTQ..... | YYGQQAG.VL | QEARVPI... | ..ISNDVCNG |
| Elastase IIIa | NKTP.CYITG | WGRLYT.... | NGP.LPD.KL | QQARLPV... | ..VDYKHCSR |
| Elastase IIIb | NETP.CYITG | WGRLYT.... | NGP.LPD.KL | QEALLPV... | ..VDYEHCSR |
| Elastase IIa | NNYP.CYVTG | WGRLQT.... | NGA.VPD.VL | QQGRLLV... | ..VDYATCSS |

|  | 151 |  |  |  | 200 |
| --- | --- | --- | --- | --- | --- |
| Elastase IIb | NNYP.CYVTG | WGRLQT.... | NGA.LPD.DL | KQGRLLV... | ..VDYATCSS |
| Chymotrypsin B | AGTL.CATTG | WGKTKY.... | NANKTPD.KL | QQAALPL... | ..LSNAECKK |
| Alpha Tryptase | PGMP.CWVTG | WGDVDN.... | DEPLPPPFPL | KQVKVPI... | ..MENHICDA |
| Beta Tryptase | PGMP.CWVTG | WGDVDN.... | DERLPPPFPL | KQVKVPI... | ..MENHICDA |
| Factor XI | IYTD.CWVTG | WGYRKL.... | RDKIQN..TL | QKAKIPL... | ..VTNEECQK |
| Plasma Kallikrein | IYTN.CWVTG | WGFSKE.... | KGEIQN..IL | QKVNIPL... | ..VTNEECQK |
| Acrosin | RGSQSCWVAG | WGYIEE.... | KAP.RPSSIL | MEARVDL... | ..IDLDLCNS |
| Trypsin I | .GTK.CLISG | WGNTAS.... | SGADYPD.EL | QCLDAPV... | ..LSQAKCEA |
| Trypsin II | .GTE.SLISG | WGNTLS.... | SGADYPD.EL | QCLDAPV... | ..LSQAECEA |
| Trypsin III | .GTE.CLISG | WGNTLS.... | FGADYPD.EL | KCLDAPV... | ..LREAECKA |
| Tissue Kallikrein 2 | .GTT.CYASG | WGSIEP.... | EEFLRPR.SL | QCVSLHL... | ..LSNDMCAR |
| PSA | .GTT.CYASG | WGSIEP.... | EEFLTPK.KL | QCVDLHV... | ..ISNDVCAQ |
| Tissue Kallikrein 1 | .GST.CLASG | WGSIEP.... | ENFSFPD.DL | QCVDLKI... | ..LPNDECEK |
| Granzyme B | PGQT.CSVAG | WGQTAP.... | LG.KHSH.TL | QEVKMTV... | ..QEDRKCES |
| T-cell Granzyme / Cathepsin G | PGQL.CSVAG | WG.YVS.... | MS.TLAT.TL | QEVLLTV... | ..QKDCQCER |
| Complement Factor D | PGTL.CTVAG | WGR.VS.... | MR.RGTD.TL | REVQLRV... | ..QRDRQCLR |
| Granzyme A | PGTL.CDVAG | WGIVNH.... | AG.RRPD.SL | QHVLLPV... | ..LDRATCRL |
| Complement Factor I | PGTM.CQVAG | WGRTHN.... | SA.SWSD.TL | REVNITI... | ..IDRKVCND |
|  | QPNDTCIVSG | WGREKDNERV | FSLQWGEVKL | ISNCSKF... | ..YGNRFYEK |

```
                      201                                                         250
Complement Factor B   RDAQYAPGYD KVKDISEVVT PRFLCTGGVS PYADPNTCRG DSGGPLIVHK
     Complement C2    VVSQEKTMFP NLTDVREVVT DQFLCSGTQ. .EDESPCKG ESGGAVFLER
          Medullasin  .......... .......... ........SL CRRSNVCTLV RGRQAGVCFG DSGSPLVCNG
         Myeloblastin .......... .......... ........FF CRPHNICTFV PRRKAGICFG DSGGPLICDG
     Complement C1S   VKVEKPTADA EAYVFTPNMI CAG....GEK G...MDSCKG DSGGAFAVQD
     Complement C1R   WLRGKNRMD. ...VFSQNMF CAGH...PSL K...QDACQG DSGGVFAVRD
            Factor X  ....SSSFI. ....ITQNMF CAGY...DTK Q...EDACQG DSGGPHV..T
            Factor IX ....STKFT. ....IYNNMF CAGF...HEG G...RDSCQG DSGGPHV..T
           Factor VII ....QSRKVG DSPNITEYMF CAGY...SDG S...KDSCKG DSGGPHA..T
            Protein C ....VMSNM. ....VSENML CAGI...LGD R...QDACEG DSGGPMV..A
             Thrombin ....STRI.. ....RITDNMF CAGYKPDEGK R...GDACEG DSGGPFVMKS
                 u-PA PHYYGS.... ....EVTTKML CAADPQWKT. .....DSCQG DSGGPLVCSL
                 t-PA QHLLNR.... ....TVTDNML CAGDTRSGGP QANLHDACQG DSGGPLVCLN
          Factor XII  PDVHGS.... ....SILPGML CAGFLEGGI. .....DACQG DSGGPLVCED
      Apolipoprotein A YKY....... .......... I CAEHLARGT. .....DSCQG DSGGPLVCFE
              Plasmin YEFLNG.... ....RVQSTEL CAGHLAGGT. .....DSCQG DSGGPLVCFE
               Hepsin ADFYGN.... ....QIKPKMF CAGYPEGGI. .....DACQG DSGGPFVCED
        Elastase IIIa WNWWGS.... ....TVKKTMV CAG.GY.IR. .....SGCNG DSGGPLNCPT
        Elastase IIIb WNWWGS.... ....SVKKTMV CAG.GD.IR. .....SGCNG DSGGPLNCPT
        Elastase IIa  SAWWGS.... ....SVKTSMI CAG.GDGVI. .....SSCNG DSGGPLNCQA
```

```
                        201                                                     250
Elastase IIb        SGWWGS.... ...TVKTNMI CAG.GDGVI. ......CTCNG DSGGPLNCQA
Chymotrypsin B      S..WGR.... ...RITDVMI CAG.ASGV.. ......SSCMG DSGGPLVCQ.
Alpha Tryptase      KYHLGAYTGD DVRIIRDDML CAG..NSQR. ......DSCKG DSGGPLVCKV
Beta Tryptase       KYHLGAYTGD DVRIVRDDML CAG..NTRR. ......DSCQG DSGGPLVCKV
Factor XI           RYR....... .GHKITHKMI CAGYREGGK. ......DACKG DSGGPLSCKH
Plasma Kallikrein   RYQ....... .DYKITQRMV CAGYKEGGK. ......DACKG DSGGPLVCKH
Acrosin             TQWYNG.... ...RVQPTNV CAGYPVGKI. ......DTCQG DSGGPLMCKD
Trypsin I           .....S.... YPGKITSNMF CVGFLEGGK. ......DSCQG DSGGPVVCNG
Trypsin II          .....S.... YPGKITNNMF CVGFLEGGK. ......DSCQG DSGGPVVSNG
Trypsin III         .....S.... CPGKITNSMF CVGFLEGGK. ......DSWKR DSGGPVVCNG
Tissue Kallikrein 2 .....A.... YSEKVTEFML CAGLWTGGK. ......DTCGG DSGGPLVCNG
PSA                 .....V.... HPQKVTKFML CAGRWTGGK. ......STCSG DSGGPLVCNG
Tissue Kallikrein 1 .....A.... HVQKVTDFML CVGHLEGGK. ......DTCVG DSGGPLMCDG
Granzyme B          DLRHY..... YDSTIEL... CVGDPEIKK. ......TSFKG DSGGPLVCNK
T-cell Granzyme     LFHGN..... YSRATEI... CVGDPKKTQ. ......TGFKG DSGGPLVCKD
Cathepsin G         IF.GS..... YDPRRQI... CVGDRRERK. ......AAFKG DSGGPLLCNN
Complement Factor D YD........ .....VLRLM CAESNR..R. ......DSCKG DSGGPLVCGG
Granzyme A          RNHYN..... FNPVIGMNMV CAGSLRGGR. ......DSCNG DSGSPLLCEG
Complement Factor I .......... ........EME CAGTYDGSI. ......DACKG DSGGPLVCMD
```

```
                         251                                                         300
Complement Factor B   RS.....RFIQ VGVISWGVVD VC...KNQKR QKQVP....A HARDFHINLF
    Complement C2    RF.....RFFQ VGLVSWGLYN PCLGSADKNS RKRAPRSKVP PPRDFHINLF
        Medullasin   ..........LI HGIASFVR.G GCASGLYPDA FAPVA.....
       Myeloblastin  ..........II QGIDSFVI.W GCATRLFPDF FTRVA.....
    Complement C1s   PN.DKTKFYA AGLVSWGP.. QCG.T..YGL YTRVK.....
    Complement C1R   PN.TD.RWVA TGIVSWGI.. GCSRG..YGF YTKVL.....
         Factor X    RF.KDTYFV. TGIVSWGE.. GCARKGKYGI YTKVT.....
         Factor IX   EV.EGTSFL. TGIISWGE.. ECAMKGKYGI YTKVS.....
        Factor VII   HY.RGTWYL. TGIVSWGQ.. GCATVGHFGV YTRVS.....
         Protein C   SF.HGTWFL. VGLVSWGE.. GCGLLHNYGV YTKVS.....
         Thrombin    PF.NNRWYQ. MGIVSWGE.. GCDRDGKYGF YTHVF.....
            u-PA     Q.G...RMTL TGIVSWGR.. GCALKDKPGV YTRVS.....
            t-PA     D.G...RMTL VGIISWGL.. GCGQKDVPGV YTKVT.....
        Factor XII   Q.AAERRLIL QGIISWGS.. GCGDRNKPGV YTDVA.....
     Apolipoprotein A ...KDKYIL QGVTSWG..L GCARPNKPGV YARVS.....
          Plasmin    ...KDKYIL QGVTSWG..L GCARPNKPGV YVRVS.....
          Hepsin     SISRTPRWRL CGIVSWG..T GCALAQKPGV YTKVS.....
       Elastase IIIa E...DGGWQV HGVTSFVSAF GCNFIWKPTV FTRVS.....
       Elastase IIIb E...DGGWQV HGVTSFVSAF GCNTRRKPTV FTRVS.....
       Elastase IIa  S...DGRWQV HGIVSFGSRL GCNYYHKPSV FTRVS.....
```

FIG. 1L

```
                   251                                                    300
Elastase IIb       S...DGRWEV HGIGSLTSVL GCNYYYKPSI FTRVS.............
Chymotrypsin B     K...DGAWTL VGIVSWGSDT CST..SSPGV YARVT.............
Alpha Tryptase     ....NGTWLQ AGVVSWDE.. GCAQPNRPGI YTRVT.............
Beta Tryptase      ....NGTWLQ AGVVSWGE.. GCAQPNRPGI YTRVT.............
Factor XI          ....NEVWHL VGITSWGE.. GCAQRERPGV YTNVV.............
Plasma Kallikrein  ....NGMWRL VGITSWGE.. GCARREQPGV YTKVA.............
Acrosin            S..KESAYVV VGITSWG..V GCALAKRPGI YTATW.............
Trypsin I          .........QL QGVVSWGDG. .CAQKNKPGV YTKV..............Y
Trypsin II         .........EL QGIVSWGYG. .CAQKNRPGV YTKV..............Y
Trypsin III        .........QL QGVVSWGHG. .CAWKNRPGV YTKV..............Y
Tissue Kallikrein 2 ........VL QGITSWGPE. PCALPEKPAV YTKV..............V
PSA                ........VL QGITSWGSE. PCALPERPSL YTKV..............V
Tissue Kallikrein 1 ........VL QGVTSWGYV. PCGTPNKPSV AVRV..............L
Granzyme B         ........VA QGIVSYGRNN GMP....PRA CTKVS.............
T-cell Granzyme    ........VA QGILSYGNKK GTP....PGV YIKVS.............
Cathepsin G        ........VA HGIVSYGKSS GVP....PEV FTRVS.............
Complement Factor D ........VL EGVVTSG.SR VCGNRKKPGI YTRVA.............
Granzyme A         ........VF RGVTSFGLEN KCGDPRGPGV YILLS..............K
Complement Factor I ANNVTYVW.. .GVVSWGE.. NCGKPEFPGV YTKVA.............
```

```
                    301                                              350
Complement Factor B  QVLPWLKEKL QDEDLGFL..  .......... .......... ..........
       Complement C2  RMQPWLRQHL GDVLNFLPL.  .......... .......... ..........
          Medullasin  QFVNWIDSII QRSEDNPCPH PRDPDPASRT H......... ..........
         Myeloblastin LYVDWIRSTL RRVEAKGRP.  .......... .......... ..........
      Complement C1s  NYVDWIMKTM QENSTPRED.  .......... .......... ..........
      Complement C1r  NYVDWIKKEM EEED......  .......... .......... ..........
            Factor X  AFLKWIDRSM KTRGLPKAKS HAPEVITSSP LK........ ..........
            Factor IX RYVNWIKEKT KLT.......  .......... .......... ..........
           Factor VII QYIEWLQKLM RSEPRPGVLL RAPFP..... .......... ..........
           Protein C  RYLDWIHGHI RDKEAPQKSW AP........ .......... ..........
            Thrombin  RLKKWIQKVI DQFGE.....  .......... .......... ..........
                u-PA  HFLPWIRSHT KEENGLAL..  .......... .......... ..........
                t-PA  NYLDWIRDNM RP........  .......... .......... ..........
           Factor XII YYLAWIREHT VS........  .......... .......... ..........
     Apolipoprotein A RFVTWIEGVM RNN.......  .......... .......... ..........
             Plasmin  RFVTWIEGVM RNN.......  .......... .......... ..........
              Hepsin  DFREWIFQAI KTHSEASGMV TQL....... .......... ..........
        Elastase IIIa AFIDWIEETI ASH.......  .......... .......... ..........
        Elastase IIIb AFIDWIEETI ASH.......  .......... .......... ..........
        Elastase IIa  NYIDWINSVI ANN.......  .......... .......... ..........
        Elastase IIb  NYNDWINSVI ANN.......  .......... .......... ..........
        Chymotrypsin B KLIPWVQKIL AAN.......  .......... .......... ..........
```

FIG.1M

```
                        301                                                          350
   Alpha Tryptase      YYLDWIHHYV PKKP...... .......... .......... .......... ..........
    Beta Tryptase      YYLDWIHHYV PKKP...... .......... .......... .......... ..........
       Factor XI       EYVDWILEKT QAV....... .......... .......... .......... ..........
 Plasma Kallikrein     EYMDWILEKT QSSDGKAQMQ SPA....... .......... .......... ..........
         Acrosin       PYLNWIASKI GSNALRMIQS ATPPPPTTRP PPIRPPFSHP ISAHLPWYFQ
       Trypsin I       NYVKWIKNTI AANS...... .......... .......... .......... ..........
      Trypsin II       NYVDWIKDTI AANS...... .......... .......... .......... ..........
     Trypsin III       NYVDWIKDTI AANS...... .......... .......... .......... ..........
Tissue Kallikrein 2    HYRKWIKDTI AANP...... .......... .......... .......... ..........
           PSA         HYRKWIKDTI VANP...... .......... .......... .......... ..........
Tissue Kallikrein 1    SYVKWIEDTI AENS...... .......... .......... .......... ..........
       Granzyme B      SFVHWIKKTM KRY....... .......... .......... .......... ..........
   T-cell Granzyme     HFLPWIKRTM KRL....... .......... .......... .......... ..........
      Cathepsin G      SFLPWIRTTM RSFKLLDQME TPL....... .......... .......... ..........
Complement Factor D    TYAAWIDHVL .......... .......... .......... .......... ..........
      Granzyme A       KHLNWIIMTI KGAV...... .......... .......... .......... ..........
Complement Factor I    NYFDWISYHV GRPFISQYNV .......... .......... .......... ..........
                        351                                                          400
         Acrosin       PPPRPLPPRP PAAQPPPPPS PPPPPPPPAS PLPPPPPPPP PTPSSTTKLP
                        401             442
         Acrosin       QGLSFAKRLQ QLIEVLKGKT YSDGKNHYDM ETTELPELTS TS
```

FIG. 1N

```
              1
Antiplasmin   MALLWGLLVL SWSCLQGPCS VFSPVSAMEP LGRQLTSGPN QEQVSPLTLL
                                                                    50

51
Antiplasmin   KLGNQEPGGQ TALKSPPGVC SRDPTPEQTH RLARAMMAFT ADLFSLVAQT
Ovalbumin     ---------- ---------- ---------- -------G   SIGAASMEFC FDVFKELKVH
                                                                    100

101
Antiplasmin   STCPNLILSP LSVALALSHL ALGAQNHTLQ RLQQVLHAGS GP--------
Ovalbumin     HANENIFYCP IAIMSALAMV YLGAKDSTRT QINKVVRFDK LPGFGDSIEA
                                                                    150

151
Antiplasmin   ---------- CLPHLLSRLC QDLGPGAFRL AARMYLQKGF PIKEDFLEQS
Ovalbumin     QCGTSVNVHS SLRDILNQIT KPNDVYSFSL ASRLYAEERY PILPEYLQCV
                                                                    200

201
Antiplasmin   EQLF--GAKP VSLTGKQEDD LANINQWVKE ATEGKIQEFL S--GLPEDTV
Ovalbumin     KELYRGGLEP INFQTAADQA RELINSWVES QTNGIIRNVL QPSSVDSQTA
                                                                    250

251
Antiplasmin   LLLLNAIHFQ GFWRNKFDPS LTQRDSFHLD EQFTVPVEMM -QARTYPLRW
Ovalbumin     MVLVNAIVFK GLWEKAFKDE DTQAMPFRVT EQESKPVQMM YQIGLFRVAS
                                                                    300
```

FIG.4A

```
                            301                                                               350
Antiplasmin     FLLEQPEIQV AHFPFKNNMS FVVLVPTHFE WNVSQVLANL SWDTLHPPLV
Ovalbumin       MASEKMKILE LPF-ASGTMS MLVLLPDEVS -GLEQLESII NFEKLTEWTS 351                                                               400
Antiplasmin     WE----RPTK VRLPKLYLKH QMDLVATLSQ LGLQELF-QA PDLRGIS-EQ
Ovalbumin       SNVMEERKIK VYLPRMKMEE KYNLTSVLMA MGITDVFSSS ANLSGISSAE P CKARII
                BBTI Loop                                                                     450
                            401
Antiplasmin     SLVVSGVQHQ STLELSEVGV EAAAATSIAM SRMSLSS-FS VNRPFLFFIF
Ovalbumin       SLKISQAVHA AHAEINEAGR EVVGSAEAGV DAASVSEEFR ADHPFLFCIK 451                                                               500
Antiplasmin     EDTTGLPLFV GSVRNPNPSA PRELKEQQDS PGNKDFLQSL KGFPRGDKLF
Ovalbumin       HIATNAVLFF GRCVSP 501                521
Antiplasmin     GPDLKLVPPM EEDYPQFGSP K
```

FIG.4B

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 690 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (ix) FEATURE:
      (A) NAME/KEY: CDS
      (B) LOCATION: 1..690
      (D) OTHER INFORMATION: /partial
         /codon_start= 1
         /function= "encodes plasmin protease domain"
         /product= "nucleotide with corresponding /number= 1

(xi) SEQUENCE DESCRIPTION: SEQ ID NO:1:

| | | | | | | | | | | | | | | | | |
|---|---|---|---|---|---|---|---|---|---|---|---|---|---|---|---|---|
| GTT | GTA | GGG | GGG | TGT | GTG | GCC | CAC | CCA | CAT | TCC | TGG | CCC | TGG | CAA | GTC | 48 |
| Val | Val | Gly | Gly | Cys | Val | Ala | His | Pro | His | Ser | Trp | Pro | Trp | Gln | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AGT | CTT | AGA | ACA | AGG | TTT | GGA | ATG | CAC | TTC | TGT | GGA | GGC | ACC | TTG | ATA | 96 |
| Ser | Leu | Arg | Thr | Arg | Phe | Gly | Met | His | Phe | Cys | Gly | Gly | Thr | Leu | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| TCC | CCA | GAG | TGG | GTG | TTG | ACT | GCT | GCC | CAC | TGC | TTG | GAG | AAG | TCC | CCA | 144 |
| Ser | Pro | Glu | Trp | Val | Leu | Thr | Ala | Ala | His | Cys | Leu | Glu | Lys | Ser | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| AGG | CCT | TCA | TCC | TAC | AAG | GTC | ATC | CTG | GGT | GCA | CAC | CAA | GAA | GTG | AAT | 192 |
| Arg | Pro | Ser | Ser | Tyr | Lys | Val | Ile | Leu | Gly | Ala | His | Gln | Glu | Val | Asn | |
| | 50 | | | | | 55 | | | | | 60 | | | | | |

| | | | | | | | | | | | | | | | | |
|---|---|---|---|---|---|---|---|---|---|---|---|---|---|---|---|---|
| CTC | GAA | CCG | CAT | GGT | CAG | GAA | ATA | GAA | GTG | TCT | AGG | CTG | TTC | TTG | GAG | 240 |
| Leu | Glu | Pro | His | Gly | Gln | Glu | Ile | Glu | Val | Ser | Arg | Leu | Phe | Leu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CCC | ACA | CGA | AAA | GAT | ATT | GCC | TTG | CTA | AAG | CTA | AGC | AGT | CCT | GCC | GTC | 288 |
| Pro | Thr | Arg | Lys | Asp | Ile | Ala | Leu | Leu | Lys | Leu | Ser | Ser | Pro | Ala | Val | |
| | | | 85 | | | | | 90 | | | | | 95 | | | |

| | | | | | | | | | | | | | | | | |
|---|---|---|---|---|---|---|---|---|---|---|---|---|---|---|---|---|
| ATC | ACT | GAC | AAA | GTA | ATC | CCA | GCT | TGT | CTG | CCA | TCC | CCA | AAT | TAT | GTG | 336 |
| Ile | Thr | Asp | Lys | Val | Ile | Pro | Ala | Cys | Leu | Pro | Ser | Pro | Asn | Tyr | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| GTC | GCT | GAC | CGG | ACC | GAA | TGT | TTC | ATC | ACT | GGC | TGG | GGA | GAA | ACC | CAA | 384 |
| Val | Ala | Asp | Arg | Thr | Glu | Cys | Phe | Ile | Thr | Gly | Trp | Gly | Glu | Thr | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| GGT | ACT | TTT | GGA | GCT | GGC | CTT | CTC | AAG | GAA | GCC | CAG | CTC | CCT | GTG | ATT | 432 |
| Gly | Thr | Phe | Gly | Ala | Gly | Leu | Leu | Lys | Glu | Ala | Gln | Leu | Pro | Val | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| GAG | AAT | AAA | GTG | TGC | AAT | CGC | TAT | GAG | TTT | CTG | AAT | GGA | AGA | GTC | CAA | 480 |
| Glu | Asn | Lys | Val | Cys | Asn | Arg | Tyr | Glu | Phe | Leu | Asn | Gly | Arg | Val | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TCC | ACC | GAA | CTC | TGT | GCT | GGG | CAT | TTG | GCC | GGA | GGC | ACT | GAC | AGT | TGC | 528 |
| Ser | Thr | Glu | Leu | Cys | Ala | Gly | His | Leu | Ala | Gly | Gly | Thr | Asp | Ser | Cys | |
| | | | 165 | | | | | 170 | | | | | 175 | | | |

| | | | | | | | | | | | | | | | | |
|---|---|---|---|---|---|---|---|---|---|---|---|---|---|---|---|---|
| CAG | GGT | GAC | AGT | GGA | GGT | CCT | CTG | GTT | TGC | TTC | GAG | AAG | GAC | AAA | TAC | 576 |
| Gln | Gly | Asp | Ser | Gly | Gly | Pro | Leu | Val | Cys | Phe | Glu | Lys | Asp | Lys | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| ATT | TTA | CAA | GGA | GTC | ACT | TCT | TGG | GGT | CTT | GGC | TGT | GCA | CGC | CCC | AAT | 624 |
| Ile | Leu | Gln | Gly | Val | Thr | Ser | Trp | Gly | Leu | Gly | Cys | Ala | Arg | Pro | Asn | |
| | | | 195 | | | | | 200 | | | | | 205 | | | |

| | | | | | | | | | | | | | | | | |
|---|---|---|---|---|---|---|---|---|---|---|---|---|---|---|---|---|
| AAG | CCT | GGT | GTC | TAT | GTT | CGT | GTT | TCA | AGG | TTT | GTT | ACT | TGG | ATT | GAG | 672 |
| Lys | Pro | Gly | Val | Tyr | Val | Arg | Val | Ser | Arg | Phe | Val | Thr | Trp | Ile | Glu | |
| | | 210 | | | | | 215 | | | | | 220 | | | | |

| | | | | | |
|---|---|---|---|---|---|
| GGA | GTG | ATG | AGA | AAT | AAT | 690 |
| Gly | Val | Met | Arg | Asn | Asn | |
| 225 | | | | 230 | | |

(2) INFORMATION FOR SEQ ID NO:2:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO:2:

Val Val Gly Gly Cys Val Ala His Pro His Ser Trp Pro Trp Gln Val
1               5                   10                  15

```
Ser Leu Arg Thr Arg Phe Gly Met His Phe Cys Gly Gly Thr Leu Ile
             20                  25                  30

Ser Pro Glu Trp Val Leu Thr Ala Ala His Cys Leu Glu Lys Ser Pro
         35                  40                  45

Arg Pro Ser Ser Tyr Lys Val Ile Leu Gly Ala His Gln Glu Val Asn
     50                  55                  60

Leu Glu Pro His Gly Gln Glu Ile Glu Val Ser Arg Leu Phe Leu Glu
 65                  70                  75                  80

Pro Thr Arg Lys Asp Ile Ala Leu Leu Lys Leu Ser Ser Pro Ala Val
                 85                  90                  95

Ile Thr Asp Lys Val Ile Pro Ala Cys Leu Pro Ser Pro Asn Tyr Val
                100                 105                 110

Val Ala Asp Arg Thr Glu Cys Phe Ile Thr Gly Trp Gly Glu Thr Gln
                115                 120                 125

Gly Thr Phe Gly Ala Gly Leu Leu Lys Glu Ala Gln Leu Pro Val Ile
 130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
            195                 200                 205

Lys Pro Gly Val Tyr Val Arg Val Ser Arg Phe Val Thr Trp Ile Glu
    210                 215                 220

Gly Val Met Arg Asn Asn
225                 230

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: misc_feature
        (B) LOCATION: 1..24
        (D) OTHER INFORMATION: /function= "MUTAGENESIS PRIMER FOR A1"
                               /product= "SYNTHETIC DNA"

(xi) SEQUENCE DESCRIPTION: SEQ ID NO:3:

GGTGCCTCCA CAATTGTGCA TTCC                                              24

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..27
        (D) OTHER INFORMATION: /function= "MUTAGENESIS PRIMER FOR A3"
```

/product= "SYNTHETIC DNA"

(xi) SEQUENCE DESCRIPTION: SEQ ID NO:4:

GTTCGAGATT CACTTTTTGG TGTGCAC                                                    27

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /function= "MUTAGENESIS PRIMER FOR A4"
                               /product= "SYNTHETIC DNA"

(xi) SEQUENCE DESCRIPTION: SEQ ID NO:5:

CTTGGGGACT TCTTCAAGCA GTGG                                                       24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /function= "MUTAGENESIS PRIMER USED
                                           FOR A5"
                               /product= "SYNTHETIC DNA"

(xi) SEQUENCE DESCRIPTION: SEQ ID NO:6:

CTCGTACGAA GCAGGACTTG CCAG                                                       24

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..27
        (D) OTHER INFORMATION: /function= "MUTAGENESIS PRIMER
                                           FOR A12"
                               /product= "SYNTHETIC DNA"

(xi) SEQUENCE DESCRIPTION: SEQ ID NO:7:

CCAAACCTTG TTTCAAGACT GACTTGC                                                    27

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear -continued

```
    (ii) MOLECULE TYPE: cDNA (ix) FEATURE:
          (A) NAME/KEY: misc_feature
          (B) LOCATION: 1..24
          (D) OTHER INFORMATION: /function= "MUTAGENESIS PRIMER
                                            FOR A14"
                                 /product= "SYNTHETIC DNA"

(xi) SEQUENCE DESCRIPTION: SEQ ID NO:8:

CTTGGGGACT TGGCTAGACA GTGG                                              24

(2) INFORMATION FOR SEQ ID NO:9:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: misc_feature
          (B) LOCATION: 1..25
          (D) OTHER INFORMATION: /function= "MUTAGENESIS PRIMER
                                            FOR A15"
                                 /product= "SYNTHETIC DNA"

(xi) SEQUENCE DESCRIPTION: SEQ ID NO:9:

CTTGGGGACT TCCTTAGACA GTGGG                                             25

(2) INFORMATION FOR SEQ ID NO:10:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: misc_feature
          (B) LOCATION: 1..27
          (D) OTHER INFORMATION: /function= "MUTAGENESIS PRIMER
                                            FOR A16"
                                 /product= "SYNTHETIC DNA"

(xi) SEQUENCE DESCRIPTION: SEQ ID NO:10:

GTTCGAGATT CACTGCTTGG TGTGCAC                                           27
```

MODIFIED PLASMIN PRECURSORS WITH RESISTANCE TO INHIBITORS OF PLASMIN

MODIFIED PROTEASES

This application is a continuation of application Ser. No. 08/379,621, filed Feb. 3, 1995, now U.S. Pat. No. 5,645,833 which is a national stage of PCT/GB93/01632 filed on Aug. 3, 1993.

The present invention relates to serine proteases of the chymotrypsin superfamily which have been modified so that they exhibit resistance to serine protease inhibitors. The invention also relates to the precursors of such compounds, their preparation, to nucleic acid coding for them and to their pharmaceutical use.

Serine proteases are endopeptidases which use serine as the nucleophile in peptide bond cleavage. There are two known superfamilies of serine proteases and these are the chymotrypsin superfamily and the Streptomyces subtilisin superfamily (Barrett, A. J., in: *Proteinase Inhibitors*, Ed. Barrett, A. J. et al., Elsevier, Amsterdam, pp 3–22 (1986) and James, M. N. G., in: *Proteolysis and Physiological Regulation*, Ed. Ribbons, D. W. et al, Academic Press, New York, pp 125–142 (1976)).

The present invention is particularly concerned with serine proteases of the chymotrypsin superfamily which includes such compounds as plasmin, tissue plasminogen activator (t-PA), urokinase-type plasminogen activator (u-PA), trypsin, chymotrypsin, granzyme, elastase, acrosin, tonin, myeloblastin, prostate-specific antigen (PSA), gamma-renin, tryptase, snake venom serine proteases, adipsin, protein C, cathepsin G, complement components C1R, C1S and C2, complement factors B, D and I, chymase, hepsin, medullasin and proteins of the blood coagulation cascade including kallikrein, thrombin, and Factors VIIa, IXa, Xa, XIa and XIIa. Members of the chymotrypsin superfamily have amino acid and structural homology of the catalytic domains, although a comparison of the sequences of the catalytic domains reveals the presence of insertions or deletions of amino acids. However, these insertions and deletions map to the surface of the folded molecule and thus do not affect the basic structure although it is likely that they contribute to the specificity of interactions of the molecule with substrates and inhibitors (Strassburger, W. et al, *FEBS Lett.*, 157, 219–223 (1983)).

Serine protease inhibitors are also well known and are divided into the following families: the bovine pancreatic trypsin inhibitor (BPTI) family, the Kazal family, the alpha-2-macroglobulin (A2M) family, the Streptomyces subtilisin inhibitor (SSI) family, the serpin family, the Kunitz family, the four-disulphide core family, the potato inhibitor family and the Bowman-Birk family.

Serine protease inhibitors inhibit their cognate serine proteases and form stable 1:1 complexes with these proteases. Structural data are available for several protease-inhibitor complexes including trypsin-BPTI, chymotrypsin-ovomucoid inhibitor and chymotrypsin-potato inhibitor (Read, R. J. et al., in: *Proteinase Inhibitors*, Ed. Barrett, A. J. et al., Elsevier, Amsterdam, pp 301–336 (1986)). A structural feature which is common to all the serine protease inhibitors is a loop extending from the surface of the molecule which contains the recognition sequence for the active site of the cognate serine protease and, in fact, there is remarkable similarity in the specific interactions between different inhibitors and their cognate serine proteases, despite the diverse sequences of the inhibitors.

The serine proteases of the chymotrypsin superfamily play an important role in human and animal physiology. Some of the most important serine protease inhibitors are those which are involved in blood coagulation and fibrinolysis. In the process of blood coagulation, a cascade of enzyme activities is involved in generating a fibrin network which forms the framework of a clot or thrombus. Degradation of the fibrin network (fibrinolysis) involves the protease inhibitor plasmin. Plasmin is formed in the body from its inactive precursor plasminogen by cleavage of the peptide bond between arginine 561 and valine 562 of plasminogen. This reaction is catalysed by t-PA or by u-PA.

If the balance between the clotting and fibrinolytic systems becomes locally disturbed, intravascular clots may form at inappropriate locations leading to conditions such as coronary thrombosis and myocardial infarction, deep vein thrombosis, stroke, peripheral arterial occlusion and embolism. A known way of treating such conditions is to administer to a patient a serine protease of the chymotrypsin superfamily or the precursor of such an enzyme. For example, t-PA, u-PA and plasminogen in the form of anisoylated plasminogen complexed with streptokinase are used in the treatment of myocardial infarction; plasminogen is used to supplement the natural circulatory plasminogen level to enhance thrombolytic therapy; and protein C is used as an antithrombotic agent. Serine proteases of the chymotrypsin superfamily, for example factors VIIa and IX, are administered for induction of blood clotting in disorders such as haemophilia. A major problem with the use of all of these agents in this type of therapy is their rapid neutralisation by serine protease inhibitors which reduces the efficiency of the therapy and increases the dose of agent required. It would therefore be advantageous to develop modified analogues of these endopeptidases which are resistant to inactivation by serine protease inhibitors whilst maintaining their activity. However, it is not easy to predict modifications which will result in increased resistance to inhibition without significant decrease in endopeptidase activity.

WO-A-9010649 discloses serine proteases of the chymotrypsin superfamily which have been modified and which are said to have increased resistance to serine protease inhibitors. The authors of that document have studied the known structure of the complex between trypsin and BPTI and have realised that, other than the amino acids in the major recognition site, the amino acids of trypsin that make direct contact with BPTI are located in the region between residues 37 and 41 and in the region between residues 210 to 213 of the polypeptide chain. The authors have then extrapolated from this on the basis that there is a high degree of structural homology between the catalytic domains of serine proteases and have suggested that mutation of a residue in any serine protease equivalent to the Tyr-39 residue in trypsin would lead to increased resistance of the modified analogue compared with the wild-type serine protease. They also suggest that inhibition resistant t-PA analogues can be made by mutation of an additional stretch of seven amino acids which occurs in tPA, but not in trypsin, adjacent to the predicted contact point at Arg-304 (equivalent to Tyr-39 of trypsin). However, although the catalytic domains of members of the chymotrypsin superfamily of serine proteases do, in general, have sequence and structural homology, Tyr-39 of trypsin is on a loop structure on the surface of the protein and, as is shown in FIG. 1, the equivalent regions of other serine proteases are highly variable within the superfamily. Indeed, this is acknowledged in WO-A-9010649. It is, therefore, by no means evident that the specific conformation of the loop in this region of the protein is conserved between different serine proteases, especially in cases where the number of residues in the loop differ, as is the case for trypsin and plasmin. Thus, although the residues in the region may be aligned sequentially because of the alignment of their flanking regions which do have similar sequences, it is not at all evident that their side-chains are in equivalent spacial locations and, therefore, residues which are equivalent in a sequence alignment are not necessarily able to form equivalent interactions in the folded protein. If plasmin is taken as an example, it can be seen from FIG. 1 that there are three hydrophobic residues (Phe-22, Met-24 and Phe-26) which could be involved in a similar hydrophobic interaction to that of Tyr-39 in the trypsin/BPTI complex. The numbering of the plasmin residues just mentioned is the numbering of SEQ ID No 2 which depicts the protease domain of plasmin. The residue designated 1 in SEQ ID No 2 is at position 562 of the mature protein. A study of FIG. 1 shows that any of these residues could be equivalent to Tyr-39 of trypsin which occurs at position 29 in the numbering system of FIG. 1. Clearly, therefore, the method described in WO-A-9010649 for designing a protease which is resistant to inhibition is not wholly reliable and it would be preferable to design inhibition resistant mutants in a different way.

The present inventors have realised that, because the serine protease inhibitors are structurally homologous in their active centre loop and form similar interactions with their cognate serine proteases (Read, R. J. et al., in: *Proteinase Inhibitors,* Ed. Barrett, A. J. et al., Elsevier, Amsterdam, pp 301–336 (1986)), mutations in any given serine protease which result in resistance to inhibition by a serine protease inhibitor may be applicable to mutations of spatially or sequentially equivalent residues in any other member of the chymotrypsin superfamily.

The interaction between enzyme and inhibitor responsible for inhibition of enzyme activity involves the catalytic site amino acids of the enzyme and the reactive site amino acids of the inhibitor. This principal interaction is stabilised by other interactions between the molecules. Although there is a comparatively large surface of interaction between the protease and the inhibitor, the protease/inhibitor complex is mainly stabilised by a few key interactions. These are exemplified by the interactions observed in the protease/inhibitor complex between trypsin and BPTI (Huber, R. et al., *J. Mol. Biol.* 89:73–101 (1974)), which serves as a model for the interaction between the catalytic domains of other serine proteases and their cognate inhibitors. In the trypsin/BPTI complex, the key residues of the protease, apart from those in the principal recognition site, which interact with the inhibitor are residues 37–41 and 210–213 (chymotrypsin numbering), with Tyr-39 being the most important. This interaction served as the basis for WO-A-9010649 in which the spatially equivalent residues in the t-PA/PAI-1 complex were identified, and inhibitor-resistant mutants were described.

In contrast to the disclosure WO-A-9010649, the present inventors have realised that the desired disruption of the protease/inhibitor interactions which lead to inhibitor resistance need not be caused by mutating the specific residues identified in that document or their equivalents in other serine proteases. Instead, residues in spacial, rather than sequential, proximity to these key residues, may be mutated resulting in a less stable complex between the protease and the inhibitor.

In a first aspect of the present invention, there is provided a modified endopeptidase of the chymotrypsin superfamily of serine proteases or a precursor of such an endopeptidase, which is resistant to serine protease inhibitors, characterised in that the modification comprises the mutation of one or more residues in close spacial proximity (other than sequential proximity) to a site of interaction between the protease and a cognate protease inhibitor In the context of this invention, the term 'precursor', when used in relation to a serine protease, refers to a protein which is cleavable by an enzyme to produce an active serine protease.

Mutations resulting in resistance to the inhibitor may induce:

i) a conformational change in the local fold of the protease such that the resulting complex with the inhibitor is less stable than the equivalent complex between the inhibitor and the wild-type protein;

ii) a change in the relative orientations of the protease and inhibitor on forming a complex such that the resulting complex is less stable than the equivalent complex between the inhibitor and the wild-type protein;

iii) a change in the steric bulk of the protease in the region of the inhibitor-binding site such that the resulting complex is less stable than the equivalent complex between the inhibitor and the wild-type protein;

iv) a change in the electrostatic potential field in the region of the inhibtor-binding site such that the resulting complex is less stable than the equivalent complex between the inhibitor and the wild-type protein; or v) any combination of the above.

The residues to be mutated need not be sequentially close to the key residues involved in the protease/inhibitor interaction, since the three-dimensional folding of the protease chain brings sequentially distant residues into spatial proximity. It is necessary to select the residues for mutation based on a model of either the protease used to generate the mutant, or of another member of the chymotrypsin superfamily of serine proteases. Where the three-dimensional structure of the protease to be mutated is not known, the selection of residues for mutation may be based either on a three-dimensional model of the protein to be mutated derived using homology modelling or other techniques, or on sequence alignments between the protein to be mutated and other members of the chymotrypsin superfamily of serine proteases with known three-dimensional structures. If sequence alignments are employed, it is not necessary to generate a three-dimensional structural model of the protease of interest in order to select residues for mutation to give inhibitor resistance, as spatial proximity to the key residues can be inferred from those proteins in the alignment with known three-dimensional structures. The spatial relationships between the residues to be mutated and the key residues in the protease/inhibitor interaction may be inferred by any appropriate method. Suitable methods are known to those skilled in the art.

The modified serine protease may be any serine protease of the chymotrypsin superfamily since all of these enzymes have a common mechanism of action. Examples of serine protease inhibitors which can be modified according to the present invention are as follows:

plasmin, tissue plasminogen activator (t-PA), urokinase-type plasminogen activator (u-PA), trypsin, chymotrypsin, granzyme, elastase, acrosin, tonin, myeloblastin, prostate-specific antigen (PSA), gamma-renin, tryptase, snake venom serine proteases, adipsin, protein C, cathepsin G, complement components C1R, C1S and C2, complement factors B, D and I, chymase, hepsin, medullasin and proteins of the blood coagulation cascade including kallikrein, thrombin, and Factors VIIa, IXa, Xa, XIa and XIIa.

However, modified analogues of plasmin, t-PA, u-PA, activated protein C, thrombin, factor VIIa, factor IXa, factor Xa, factor XIa and factor XIIa are particularly useful, as is a modified version of plasminogen, since all of these compounds can be used as fibrinolytic or thrombotic agents. An inhibition resistant plasmin analogue is particularly preferred.

The serine protease inhibitor to which the modified serine protease of the invention is resistant will obviously depend on which serine protease has been modified. In the case of plasmin, the primary physiological inhibitor is α2-antiplasmin which belongs to the serpin family of serine protease inhibitors. The reaction between plasmin and α2-antiplasmin consists of two steps: a very fast reversible reaction between the kringle 1 lysine binding site of plasmin and the carboxy-terminal region of the inhibitor, followed by a reaction between the catalytic site of plasmin and the reactive site of the inhibitor which results in the formation of a very stable 1:1 stoichiometric enzymatically inactive complex (Holmes, W. E. et al., *J. Biol. Chem.,* 262, 1659–1664 (1987)). Therefore, when the serine protease is plasmin, it is particularly useful if the serine protease inhibitor to which the plasmin is resistant is α2-antiplasmin. Plasmin is also inhibited by α2-macroglobulin and α1-antitrypsin and resistance to inhibition by these inhibitors is also useful.

From a three-dimensional model of the plasmin/antiplasmin complex, (described in Method 1), it has been determined that, in plasmin, the residues which are in close spatial proximity to the key residues of interaction between the protease and the inhibitor are residues 17–20, 44–54, 62, 154, 158, 198–213. The numbering used above is the numbering system of sequence ID No 2 which represents the protease domain of plasmin and begins at position 562 of the mature protein. In order to be resistant to inhibition by a serine protease inhibitor such as α2-antiplasmin, it is necessary to modify plasmin in one or more of these regions. Protease inhibition resistance can be induced in other serine proteases of the chymotrypsin superfamily by modifying equivalent regions of these proteins. FIG. 1 shows the sequences of the protease domains of a variety of proteases and, from a study of FIG. 1, it is clear where modifications should be made in order to induce resistance to protease inhibitors. In the numbering system of FIG. 1, the modification regions just mentioned occur at residues 17–22, 49–64, 72, 203, 214, and 264–281. The types of mutations which are suitable for inducing resistance to inhibition include single or multiple amino acid substitutions, additions or deletions. However, amino acid substitutions are particularly preferred.

In plasmin, examples of amino acid substitution mutations which result in a modified response to inhibition by α2-antiplasmin, using the numbering system of SEQ ID No 2, are Glu-62 to Lys or Ala, Ser-17 to Leu, Arg-19 to Glu or Ala, and Glu-45 to Lys, Arg or Ala. Resistance to protease inhibition can be induced in other serine proteases by making modifications at equivalent positions. The degree of resistance to inhibition may be altered by making either single or multiple mutations in the protease, or by altering the nature of the amino acid used for substitution.

In addition to the modification of the invention, the serine protease may be modified in other ways as compared to wild-type proteins. Any modifications may be made to the protein provided that it does not lose its activity.

As an alternative to a modified serine protease, it is also possible to modify a precursor of the enzyme so that the enzyme derived from the precursor will have the desired resistance to inhibition. An example of a serine protease precursor is plasminogen which is the inactive precursor of plasmin. Conversion of plasminogen to plasmin is accomplished by cleavage of the peptide bond between arginine 561 and valine 562 of plasminogen. Under physiological conditions this cleavage is catalysed by t-PA or u-PA. Cleavage of a modified plasminogen variant of the present invention will produce a plasmin variant as descried above and it is, of course, preferable that the plasminogen variant will be cleaved to produce one of the preferred plasmin variants described above.

Again, as with serine proteases, the precursors may have other modifications. Analysis of the wild-type plasminogen molecule has revealed that it is a glycoprotein composed of a serine protease domain, five kringle domains and an N-terminal sequence of 78 amino acids which may be removed by plasmin cleavage. Cleavage by plasmin involves hydrolysis of the Arg(68)–Met(69), Lys(77)–Lys (78) or Lys(78)–Val(79) bonds to create forms of plasminogen with an N-terminal methionine, lysine or valine residue, all of which are commonly designated as lys-plasminogen. Intact plasminogen is referred to as glu-plasminogen because it has an N-terminal glutamic acid residue. Glycosylation occurs on residues Asn(289) and Thr(346) but the extent and composition are variable, leading to the presence of a number of different molecular weight forms of plasminogen in the plasma. Any of the above plasminogen variants may be modified to produce a variant according to the present invention. The protein sequencing studies of Sottrup-Jensen et al (in: *Atlas of Protein Sequence and Structure* (Dayhoff, M. O., ed.) 5 suppl. 3, p. 95 (1978)) indicated that plasminogen was a 790 amino acid protein and that the site of cleavage was the Arg(560)–Val(561) peptide bond. A plasminogen variant which is suitable for modification according to the present invention is a 791 residue protein with an extra Ile at position 65 and encoded by cDNA isolated by Forsgren et al (*FEBS Letters,* 213, 254–260 (1987)). The serine protease domain of any of these plasminogen analogues can be recognised by its homology with serine proteases and on activation to plasmin is the catalytically active domain involved in fibrin degradation. The five kringle domains are homologous to those in other plasma proteins such as tPA and prothrombin and are involved in fibrin binding and thus localisation of plasminogen and plasmin to thrombi.

The plasminogen analogues of the present invention may also contain other modifications (as compared to wild-type glu-plasminogen) which may be one or more additions, deletions or substitutions. Examples of particularly suitable plasminogen analogues are disclosed in our copending applications WO-A-9109118 and GB 9222758.6 and comprise plasminogen analogues which are cleavable by an enzyme involved in blood clotting to produce active plasmin. These plasminogen analogues may, according to the present invention, be further modified so that, on cleavage, the plasmin which is produced is resistant to inhibition by serine protease inhibitors such as α2-antiplasmin. Other plasminogen analogues which may be modified to produce the plasminogen analogues of the invention are analogues in which there has been an addition, removal, substitution or alteration of one or more kringle domains. Other suitable plasminogen analogues are Lys-plasminogen variants in which the amino terminal 68, 77 or 78 amino acids have been deleted. Such variants may have enhanced fibrin binding activity as has been observed for lys-plasminogen compared to wild-type glu-plasminogen (Bok, R. A. and Mangel, W. F., *Biochemistry,* 24, 3279–3286 (1985)). Also included within the scope of the invention are plurally-modified plasminogen analogues which include one or more modifications to prevent, reduce or alter glycosylation patterns. Such analogues may have a longer half-life, reduced plasma clearance and/or higher specific activity.

The modified serine proteases and serine protease precursors of the invention can be prepared by any suitable method and, in a second aspect of the invention, there is provided a process for the preparation of such a serine protease or serine protease precursor, the process comprising coupling together successive amino acid residues and/or ligating oligopeptides. Although the proteins may, in principle, be synthesised wholly or partly by chemical means, it is preferred to prepare them by ribosomal translation, preferably in vivo, of a corresponding nucleic acid sequence. The process may further include an appropriate glycosylation step.

It is preferred to produce proteins of the invention using recombinant DNA technology. DNA encoding a naturally occurring serine protease or precursor may be obtained from a cDNA or genomic clone or may be synthesised. Amino acid substitutions, additions or deletions are preferably introduced by site-specific mutagenesis. DNA sequences encoding glu-plasminogen, lys-plasminogen, other plasminogen analogues and serine protease variants may be obtained by procedures familiar to those skilled in the art of genetic engineering.

The process for producing proteins using recombinant DNA technology will usually include the steps of inserting a suitable coding sequence into an expression vector and transfecting the vector into a suitable host cell. Therefore, in a third aspect of the invention there is provided nucleic acid coding for a modified serine protease as described above. The nucleic acid may be either DNA or RNA and may be in the form of a vector such as a plasmid, cosmid or phage. The vector may be adapted to transfect or transform prokaryotic cells, such as bacterial cells and/or eukaryotic cells, such as yeast or mammalian cells. The vector may be a cloning vector or an expression vector and comprises a cloning site and, preferably, at least one marker gene. An expression vector will additionally have a promoter operatively linked to the sequence to be inserted into the cloning in site and, preferably, a sequence enabling the protein product to be secreted.

Most of the proteins of the present invention, including molecules such as tPA, can easily be obtained by inserting the coding sequence into an expression vector as described and transfecting the vector into a suitable host cell which may be a bacterium such as E. coli, a eukaryotic microorganism such as yeast or a higher eukaryotic cell. With molecules such as plasminogen which are unusually difficult to express, it may be necessary to use a vector of the type described in our copending application, WO-A-9109118, which comprises a first nucleic acid sequence coding for the modified serine protease, operatively linked to a second nucleic acid sequence containing a strong promoter and enhancer sequence derived from human cytomegalovirus, a third nucleic acid sequence encoding a polyadenylation sequence derived from SV40 and a fourth nucleic acid sequence coding for a selectable marker expressed from an SV40 promoter and having an additional SV40 polyadenylation signal at the 3' end of the selectable marker sequence. Such a vector may either comprise a single nucleic acid molecule or a plurality of such molecules so that, for example, the first, second and third sequences may be contained in a first nucleic acid molecule and the fourth sequence may be contained in a second nucleic acid molecule. This vector is particularly useful for the expression of plasminogen and plasminogen analogues.

For any of the proteins of the invention, the vector is preferably chosen so that the protein is expressed and secreted into the cell culture medium in a biologically active form without the need for any additional biological or chemical procedures. In the case of plasminogen, this can be achieved using the vector described above.

In a further aspect of the invention there is provided a process for the preparation of nucleic acid encoding a modified serine protease which exhibits resistance to serine protease inhibitors, the process comprising coupling together successive nucleotides and/or ligating oligo- and/or poly-nucleotides.

In a further aspect of the invention, there is provided a cell transformed or transfected by a vector as described above. Suitable cells or cell lines include both prokaryotic and eukaryotic cells. A typical example of a eukaryotic cell is a bacterial cell such as *E. coli*. Suitable eukaryotic cells include yeast cells such as *Sacchromyces cerevisiae* or *Pichia pastoris*. Other examples of suitable eukaryotic cells are mammalian cells which grow in continuous culture and examples of such cells include Chinese hamster ovary (CHO) cells, mouse myeloma cell lines such as P3X63-Ag8.653 and NS0, COS cells, HeLa cells, 293 cells, BHK cells, melanoma cell lines such as the Bowes cell line, mouse L cells, human hepatoma cell lines such as HepG2, mouse fibroblasts and mouse NIH 3T3 cells. CHO cells are particularly suitable as hosts for the expression of plasminogen and plasminogen analogues. The transformation of the cells may be achieved by any convenient method but electroporation is a particularly suitable method.

For some molecules, such as plasminogen, there may be a low level of undesirable activation during culture. Therefore, in a further aspect of the invention, there is provided a eukaryotic host cell transfected or transformed with a first DNA sequence encoding a serpin-resistant serine protease and with an additional DNA sequence encoding the cognate inhibitor.

The modified serine proteases of the present invention have a variety of uses and, if the serine protease is a fibrinolytic or thrombolytic enzyme, it will be useful in a method for the treatment and/or prophylaxis of diseases or conditions caused by blood clotting, the method comprising administering to a patient an effective amount of the serine protease.

Therefore, in a further aspect of the invention, there is provided a modified serine protease according to the first aspect of the invention, which is a serine protease having fibrinolytic, thrombolytic, antithrombotic or prothrombotic properties, for use in medicine, particularly in the treatment of diseases mediated by blood clotting. Such conditions include myocardial and cerebral infarction, arterial and venous thrombosis, thromboembolism, post-surgical adhesions, thrombophlebitis and diabetic vasculopathies.

The invention also provides the use of a modified fibrinolytic, thrombolytic, antithrombotic or prothrombotic serine protease according to the first aspect of the invention in the preparation of an agent for the treatment and/or prophylaxis of diseases or conditions mediated by blood clotting. Examples of such conditions are mentioned above.

Furthermore, there is also provided a pharmaceutical or veterinary composition comprising one or more modified serine proteases of the first aspect of the invention together with a pharmaceutically and/or veterinarily acceptable carrier.

The composition may be adapted for administration by oral, topical or parenteral routes including intravenous or intramuscular injection or infusion. Suitable injectable compositions may comprise a preparation of the compound in isotonic physiological saline and/or buffer and may also include a local anaesthetic to alleviate the pain of the injection. Similar compositors may be used for infusions. If the compound is administered topically, it may be formulated as a cream, ointment or lotion in a suitable base.

The compounds of the invention may be supplied in unit dosage form, for example as a dry powder or water-free concentrate in a hermetically sealed container such as an ampoule or sachet.

The quantity of material to be administered will depend on the amount of fibrinolysis or inhibition of clotting required, the required speed of action, the seriousness of the thromboembolic position and the size of the clot. The precise dose to be administered will, because of the very nature of the condition which compounds of the invention are intended to treat, be determined by the physician. As a guideline, however, a patient being treated for a mature thrombus will generally receive a daily dose of a plasminogen analogue of from 0.01 to 10 mg/kg of body weight either by injection in for example up to 5 doses or by infusion.

The invention will now be further described by way of example only with reference to the following drawings in which:

FIGS. 1A–1N show the alignment of the catalytic domain amino acids of the chymotrypsin superfamily;

FIGS. 4A–4B show the sequence alignment of ovalbumin and α2-antiplasmin used to generate the β2-antiplasmin model.

The following examples further illustrate the invention. Examples 1 to 5 describe the expression of various plasminogen analogues from higher eukaryotic cells and example 6 describes an assay used to assess resistance to α2-antiplasmin.

EXAMPLE 1

Construction and Expression of A1 and A12

Figure 2A:
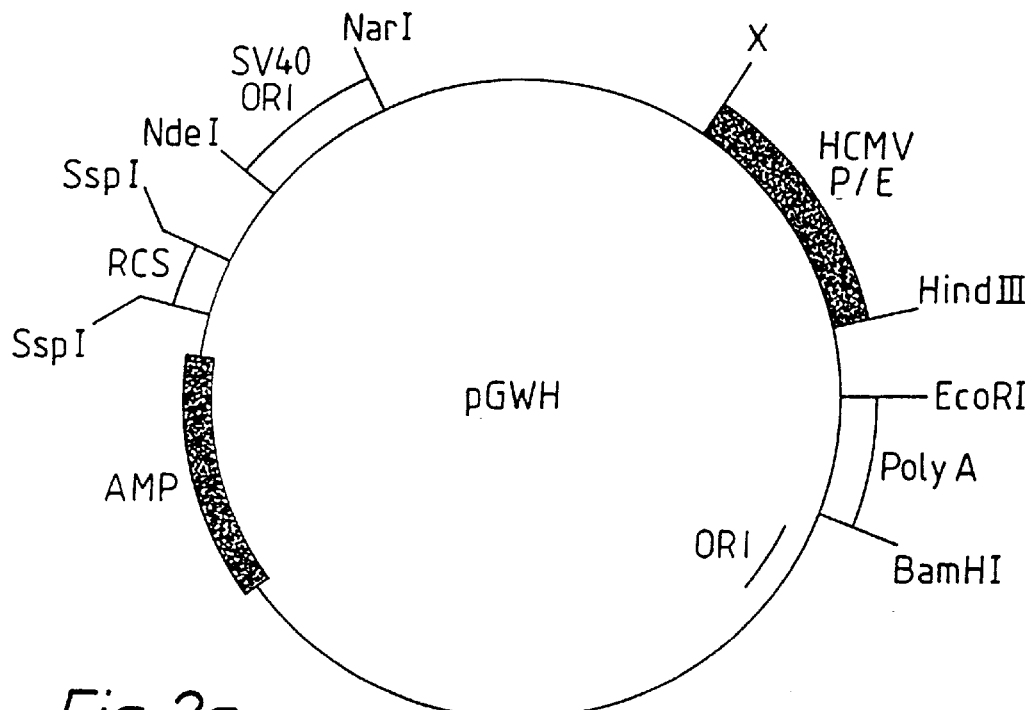
FIGS. 2A–2B show maps of the pGWH and pGWHgP vectors.
Figure 2B:
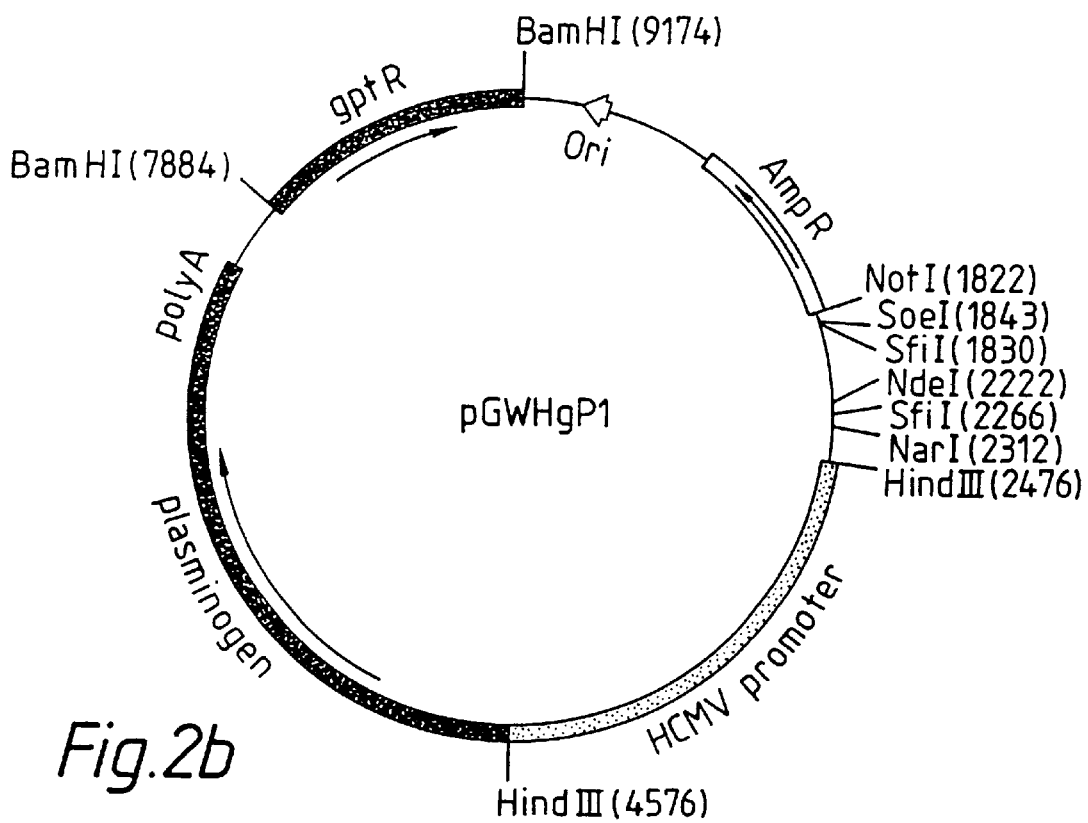

The isolation of plasminogen CDNA and construction of the vectors pGWH and pGWHgP (FIG. 2) have been described in WO-A-9109118. In pGWHgP, transcription through the plasminogen cDNA can initiate at the HCMV promoter/enhancer and the selectable marker gpt is employed.

The techniques of genetic manipulation, expression and protein purification used in the manufacture of the modified plasminogen examples to follow, are well known to those skilled in the art of genetic engineering. A description of most of the techniques can be found in one of the following laboratory manuals: "Molecular Cloning" by T. Maniatis, E. F. Fritsch and J. Sambrook published by Cold Spring Harbor Laboratory, Box 100, New York, or "Basic Methods in Molecular Biology" by L. G. Davis, M. D. Dibner and J. F. Battey published by Elsevier Science publishing Co Inc, New York.

Additional and modified methodologies are detailed in the methods section below.

Plasminogen analogues have been constructed which are designed to be resistant to inhibition by α2-antiplasmin. A1 is a plasminogen analogue in which the amino acid Phe587 is replaced by Asn. A12 is a plasminogen analogue in which the Arg-580 is replaced by Glu. The modification strategy in this example is essentially as described in WO-A-9109118 Example 3, with the mutagenesis reaction carried out on the 1.87 kb KpnI to HincII fragment of the thrombin activatable plasminogen analogue T19 cloned into the bacteriophage M13mp18. Single stranded template was prepared and the mutation made by oligonucleotide directed mutagenesis. For A1, a 24 base long oligonucleotide 5'GGTGCCTCCA-CAATTGTGCATTCC3' (SEQ. ID. 3) was used to direct the mutagenesis and for A12 a 27 base oligonucleotide was used 5' CCAAACCTTGTTTCAAGACTGACTTGC 3' (SEQ ID 7).

Plasmid DNA was introduced into CHO cells by electroporation using 800 V and 25 μF as described in the methods section below. Selective medium (250 μl/ml xanthine, 5 μg/ml mycophenolic acid, 1× hypoxanthine-thymidine (HT)) was added to the cells 24 hours post transfection and the media changed every two to three days. Plates yielding gpt-resistant colonies were screened for plasminogen production using an ELISA assay. Cells producing the highest levels of antigen were re-cloned and the best producers scaled up into flasks with production being carefully monitored. Frozen stocks of all these cell lines were laid down. Producer cells were scaled up into roller bottles to provide conditioned medium from which plasminogen protein was purified using lysine SEPHAROSE 4B. (The word SEPHAROSE is a trade mark.)

EXAMPLE 2

Construction and Expression of A3 and A16

The procedure of Example 1 was generally followed except that the mutagenesis was performed on an EcoRV to HindIII fragment (0.85 kb) containing the 3' of wild type plasminogen cloned into M13. The oligonucleotide used was a 27mer 5'GTTCGAGATTCACTTTTTGGTGTG-CAC3' (SEQ. ID. 4) which changed Glu-623 to Lys, thus changing an acidic amino acid to a basic amino acid. The resulting mutant was cloned as an EcoRV to Sphl fragment replacing the corresponding wild type sequence. The 27 base oligonucleotide 5'GTTCGAGATTCACTGCTTGGTGTG-CAC3' (SEQ ID 10) was used to change Glu-623 to Ala to produce A16.

EXAMPLE 3

Construction and Expression of A4, A14 and A15

Mutant A4 is designed to disrupt ionic interactions on the surface of plasminogen preventing binding to antiplasmin. The mutagenesis and sub-cloning strategy was as described in Example 1 using a 24 base oligonucleotide 5' CTTGGG-GACTTCTTCAAGCAGTGG3' (SEQ. ID. 5) designed to convert Glu-606 to Lys. The 24 base oligonucleotide 5' CTTGGGGACTTGGCTAGACAGTGG 3' (SEQ ID 8) was used to change Glu-606 to Ala to produce A14 and the 25 base oligonucleotide 5' CTTGGGGACTTCCTTAGA-CAGTGGG 3' (SEQ ID 9) was used to change Glu-606 to Arg to produce A15.

EXAMPLE 4

Construction and Expression of A5

Plasminogen analogue A5 was designed to alter the positioning of the Tyr 39 containing structural loop and was made generally as described in the procedure of Example 1. In A5, Ser-578 has been replaced by Leu using the 24mer 5' CTCGTACGAAGCAGGACTTGCCAG3' (SEQ. ID. 6) on the KpnI to EcoRV fragment of plasminogen in M13 as the template. The mutation was cloned directly into pGW1Hg.plasminogen using the restriction enzymes HindIII and SplI. These sites had previously been introduced at the extreme 5' end of plasminogen and at 1850 respectively via mutagenesis; the plasminogen coding sequence was not affected by this procedure.

EXAMPLE 5

Construction and Expression of Double Mutant A3A4

Plasminogen mutant A3A4 combines the two mutations A3 and A4 as described in Examples 2 and 3 respectively. Mutagenesis was performed on the EcoRV to SphI fragment of A4 cloned into M13 using the A3 mutagenesis oligonucleotide (SEQ ID4).

EXAMPLE 6

Plasmin-Antiplasmin Interaction Assays

A chromogenic assay was used to assess the resistance of the plasmin(ogen) mutants to inhibition by α2-antiplasmin. Inhibition of plasmin activity was determined by the change in the rate of cleavage of the plasmin chromogenic substrate S2251 (Quadratech, P.O. Box 167, Epsom, Surrey. KT17 2SB).

Prior to assay, the plasminogens were activated to plasmin using either urokinase for mutants in wild type plasminogen, or thrombin for thrombin activatable plasminogen mutants (WO-A-9109118). Activation of wild-type plasminogen to plasmin was achieved by incubation of the plasminogen (ca. 14 μg) with urokinase ($16.8\times10^{-3}$ U) in 1750 μl of assay buffer (50 mM Tris, 0.1 mM EDTA, 0.00005% Triton X100, 0.1% (w/v) human serum albumin, pH 8.0) at 37° C. for 5 mins. Activation of thrombin activatable plasminogen mutants to plasmin was achieved by incubation of the plasminogen (ca. 14 μg) with thrombin in 1750 μl of assay buffer at 37° C. Hirudin was added to inhibit the thrombin activity as thrombin cleaves the chromogenic substrate. Plasmin (125 μl) was mixed with 250 μl S2251 (2 mg/ml in assay buffer) and 125 μl antiplasmin (1.25 μg in assay buffer, #4032 American Diagnostica Inc. 222 Railroad Avenue, P.O. Box 1165, Greennwich, Conn. 06836-1165) or 125 μl assay buffer in a cuvette and the absorbance at 405 nM measured over time.

Figure 3:
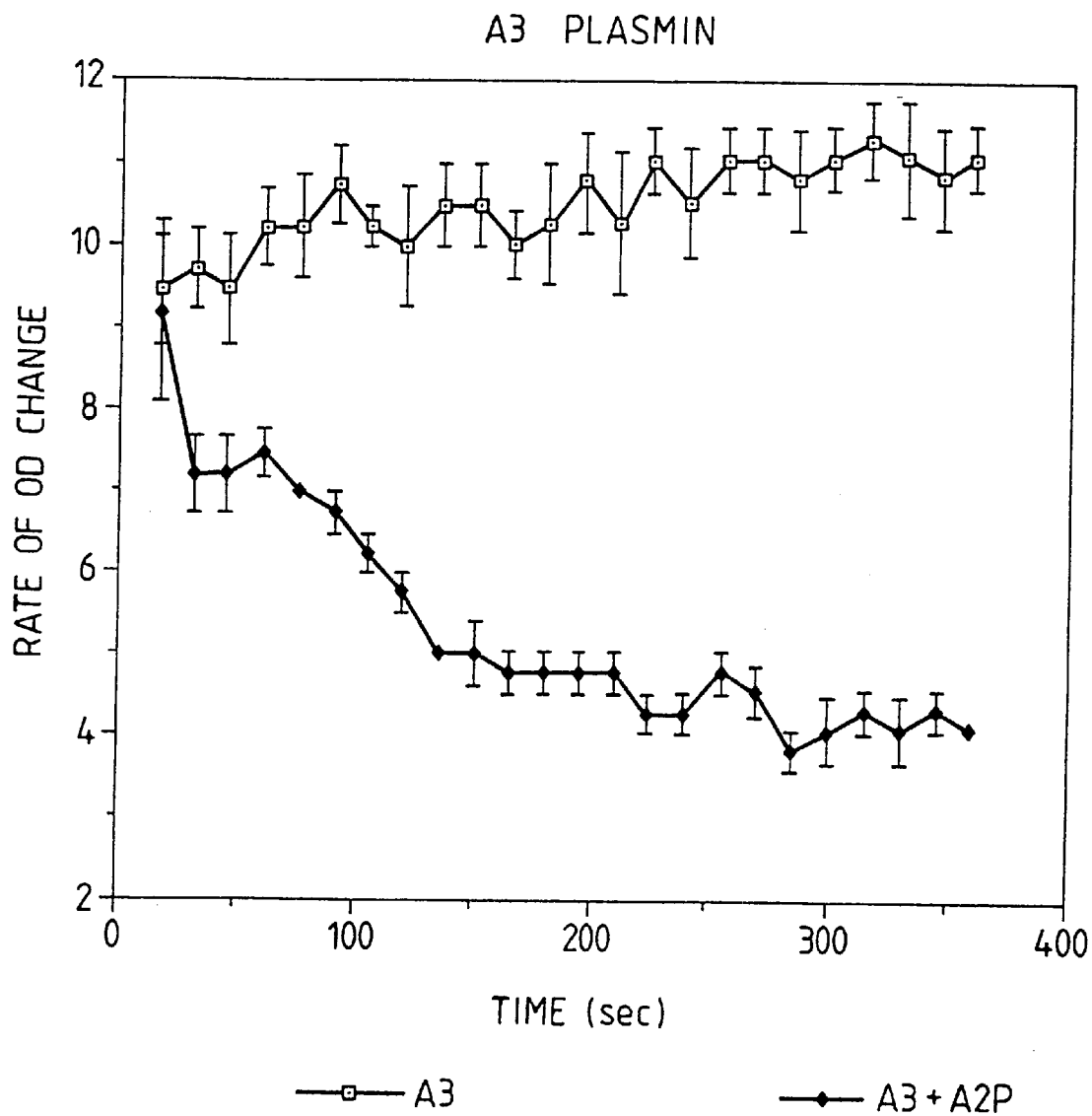
FIG. 3 shows the effect of β2-antiplasmin on the activity of plasminogen mutant A3.

A Beckman DU64 spectrophotometer and Beckman "Data Leader" data capture software were used to record absorbance at 405 nM at 1 sec intervals for 8 minutes. The Data Leader software package was used to calculate the first derivative of the data to provide the rate of change of absorbance at 405 nM against time, an estimate of active plasmin concentration against time. Wild type plasmin was rapidly inactivated by α2-antiplasmin; after only 15 seconds the plasmin was essentially inactivated. In contrast, plasminogen mutant A3 has an antiplasmin resistant phenotype and is only slowly inactivated by α2-antiplasmin with a t½ (half the rate of OD change at t=15 sec) of approximately 75 seconds (FIG. 3).

METHODS

1. Model structures were built by homology based on the x-ray structures of trypsin/BPTI.

A refined plasminogen structure was modelled by homology to thrombin using the PPACK/thrombin x-ray structure from Bode et al. (Bode, W. et al., *EMBO J.* 8:3467–3475 (1989). A refined alpha-2-antiplasmin [A2AP] structure was modelled by homology to ovalbumin using atomic co-ordinates from the Brookhaven Protein Data Bank entry 1OVA, except for the loop containing the reactive bond, which was modelled using the co-ordinates for residues 13 to 19 of BPTI from the PDB entry 2PTC. The alignment used to generate the A2AP model is shown in FIG. 4. The A2AP model described here does not include co-ordinates for the 79 N-terminal residues and 55 C-terminal residues.

Most serine-protease-directed inhibitors react with cognate enzymes according to a common, substrate-like standard mechanism (Bode, W. and Huber, R., *Eur. J. Biochem.* 204:433–451 (1992). In particular, they all possess an exposed active site-binding loop with a characteristic canonical conformation. The binding loop on the A2AP model was therefore modelled on the equivalent loop of BPTI (residues 13 to 19), using atomic co-ordinates from the PDB entry 2PTC (in which BPTI is complexed with trypsin).

The complex of A2AP and the plasmin serine protease domain was modelled using the trypsin/BPTI complex structure from PDB entry 2PTC. The A2AP model was fitted to the BPTI structure by optimising the RMS difference between the co-ordinates of the backbone atoms in the active site-binding loops of the two inhibitors. The plasmin serine protease domain model was fitted to the trypsin structure by optimising the RMS difference between the co-ordinates of the C-alpha atoms of the conserved residues in an optimal sequence alignment of the two proteins. The A2AP/plasmin complex model was then refined by energy-minimisation.

The homology modelling was performed on a Silicon Graphics Indigo workstation using the Quanta molecular modelling program from Molecular Simulations Incorporated. Sequence alignments were produced using Quanta, the GCG sequence analysis software from the University of Wisconsin (Devereux, Haeberli and Smithies, *Nucleic Acids Research* 12(1):387–395 (1984), and proprietary sequence alignment software. However, the actual method by which the homology models were built is not critical to this invention.

The trypsin and BPTI sequences used in the homology modelling were obtained from the Brookhaven Protein Data Bank atomic co-ordinate entry 2PTC, the thrombin sequence was obtained from the PPACK/thrombin co-ordinate file, the plasminogen sequence from the SWISSPROT database entry PLMN_HUMAN, and the A2AP sequence from the SWISSPROT entry A2AP_HUMAN.

2. Mung Bean Nuclease Digestion 10 units of mung bean nuclease was added to approximately 1 μg DNA which had been digested with a restriction enzyme in a buffer containing 30 mM NaOAc pH5.0, 100 mM NaCl, 2 mM ZnCl, 10% glycerol. The mung bean nuclease was incubated at 37° for 30 minutes, inactivated for 15 minutes at 67° before being phenol extracted and ethanol precipitated.

3. Oligonucleotide synthesis

The oligonucleotides were synthesised by automated phosphoramidite chemistry using cyanoethyl phosphoramidites. The methodology is now widely used and has been described (Beaucage, S. L. and Caruthers, M. H. Tetrahedron Letters 24, 245 (1981) and Caruthers, M. H. Science 230, 281–285 (1985)).

4. Purification of Oligonucleotides

The oligonucleotides were de-protected and removed from the CPG support by incubation in concentrated NH3.

Typically, 50 mg of CPG carrying 1 micromole of oligonucleotide was de-protected by incubation for 5 hours at 70° in 600 μl of concentrated NH3. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 260 nm. For gel purification 10 absorbance units of the crude oligonucleotide was dried down and resuspended in 15 μl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1× TBE and was polymerised with 0.1% ammonium persulphate and 0.025% TEMED. The gel was pre-run for 1 hr. The samples were run at 1500 V for 4–5 hours. The bands were visualised by UV shadowing and those corresponding to the full length product cut out and transferred to micro-testubes. The oligomers were eluted from the gel slice by soaking in AGEB (0.5M ammonium acetate, 0.01M magnesium acetate and 0.1% SDS) overnight. The AGEB buffer was then transferred to fresh tubes and the oligomer precipitated with three volumes of ethanol at 70° for 15 mins. The precipitate was collected by centrifugion in an Eppendorf microfuge for 10 mins, the pellet washed in 80% ethanol, the purified oligomer dried, redissolved in 1 ml of water and finally filtered through a 0.45 micron micro-filter. (The word EPPENDORF is a trade mark.) The concentration of purified product was measured by determining its absorbance at 260 nm.

5. Kinasing of Oligomers 100 pmole of oligomer was dried down and resuspended in 20 μl kinase buffer (70 mM Tris pH 7.6, 10 mM MgCl2, 1 mM ATP, 0.2 mM spermidine, 0.5 mM dithiothreitol). 10 u of T4 polynucleotide kinase was added and the mixture incubated at 37° for 30 mins. The kinase was then inactivated by heating at 70° for 10 mins.

6. Dideoxy Sequencing

The protocol used was essentially as has been described (Biggin, M. D., Gibson, T. J., Hong, G. F. P.N.A.S. 80 3963–3965 (1983). Where appropriate the method was modified to allow sequencing on plasmid DNA as has been described (Guo, L-H., Wu R Nucleic Acids Research 11 5521–5540 (1983).

7. Transformation

Transformation was accomplished using standard procedures. The strain used as a recipient in the cloning using plasmid vectors was HW87 or DH5 which has the following genotype:

araD139(ara-leu)del7697 (lacIPOZY)del74 galU galK hsdR rpsL srl recA56

RZ1032 is a derivative of $E$. $coli$ that lacks two enzymes of DNA metabolism: (a) dUTPase (dut) which results in a high concentration of intracellular dUTP, and (b) uracil N-glycosylase (ung) which is responsible for removing mis incorporated uracils from DNA (Kunkel et al, Methods in Enzymol., 154, 367–382 (1987)). Its principal benefit is that these mutations lead to a higher frequency of mutants in site directed mutagenesis. RZ1032 has the following genotype:

HfrKL16PO/45[lysA961–62), dutI, ungI, thiI, re[A], Zbd-279::Tn10, supE44

JM103 is a standard recipient strain for manipulations involving M13 based vectors.

8. Site Directed Mutagenesis

Kinased mutagenesis primer (2.5 pmole) was annealed to the single stranded template DNA, which was prepared using RZ1032 as host, (1 μg) in a final reaction mix of 10 μl containing 70 mM Tris, 10 mM MgCl2. The reaction mixture in a polypropylene micro-testube (EPPENDORF) was placed in a beaker containing 250 ml of water at 70° C. for 3 minutes followed by 37° C. for 30 minutes. The annealed mixture was then placed on ice and the following reagents added: 1 μl of 10× TM (700 mM Tris, 100 mM MgCl2 pH 7.6), 1 μl of a mixture of all 4 deoxyribonucleotide triphosphates each at 5 mM, 2 μl of T4 DNA ligase (100 u), 0.5 μl Klenow fragment of DNA polymerase and 4.5 μl of water. The polymerase reaction mixture was then incubated at 15° for 4–16 hrs. After the reaction was complete, 180 μl of TE (10 mM Tris, 1 mM EDTA pH 8.0) was added and the mutagenesis mixture stored at –20° C.

For the isolation of mutant clones the mixture was then transformed into the recipient JM103 as follows. A 5 ml overnight culture of JM103 in 2× YT (1.6% Bactotryptone, 1% Yeast Extract, 1% NaCl) was diluted 1 in a 100 into 50 ml of pre-warmed 2× YT. The culture was grown at 37° with aeration until the A600 reached 0.4. The cells were pelleted and resuspended in 0.5 vol of 50 mM CaCl2 and kept on ice for 15 mins. The cells were then re-pelleted at 4° and resuspended in 2.5 ml cold 50 mM CaCl2. For the transfection, 0.25, 1, 2, 5, 20 and 50 μl aliquots of the mutagenesis mixture were added to 200 μl of competent cells which were kept on ice for 30 mins. The cells were then heated shocked at 42° for 2 mins. To each tube was then added 3.5 ml of YT soft agar containing 0.2 ml of a late exponential culture of JM103, the contents were mixed briefly and then poured onto the surface of a pre-warmed plate containing 2× YT solidified with 1.5% agar. The soft agar layer was allowed to set and the plates then incubated at 37° overnight.

Single stranded DNA was then prepared from isolated clone as follows: Single plaques were picked into 4 ml of 2× YT that had been seeded with 10 μl of a fresh overnight culture of JM103 in 2× YT. The culture was shaken vigorously for 6 hrs. 0.5 ml of the culture was then removed and added to 0.5 ml of 50% glycerol to give a reference stock that was stored at –20°. The remaining culture was centrifuged to remove the cells and 1 ml of supernatant carrying the phage particles was transferred to a fresh EPPENDORF tube. 250 μl of 20% PEG6000, 250 mM NaCl was then added, mixed and the tubes incubated on ice for 15 mins. The phage were then pelleted at 10,000 rpm for 10 mins, the supernatant discarded and the tubes re-centrifuged to collect the final traces of PEG solution which could then be removed and discarded. The phage pellet was thoroughly resuspended in 200 μl of TEN (10 mM Tris, 1 mM EDTA, 0.3M NaOAc). The DNA was isolated by extraction with an equal volume of Tris saturated phenol. The phases were separated by a brief centrifugation and the aqueous phase transferred to a clean tube. The DNA was re-extracted with a mixture of 100 μl of phenol, 100 μl chloroform and the phases again separated by centrifugation. Traces of phenol were removed by three subsequent extractions with chloroform and the DNA finally isolated by precipitation with 2.5 volumes of ethanol at –20° overnight. The DNA was pelleted at 10,000 rpm for 10 min, washed in 70% ethanol, dried and finally resuspended in 50 μl of TE.

9. Electroporation

Chinese hamster ovary cells (CHO) or the mouse myeloma cell line p3x63-Ag8.653 were grown and harvested in mid log growth phase. The cells were washed and resuspended in PBS and a viable cell count was made. The cells were then pelleted and resuspended at 1×107 cells/ml. 40 μg of linearised DNA was added to 1 ml of cells and allowed to stand on ice for 15 mins. One pulse of 800 V/25 μF was administered to the cells using a commercially available electroporation apparatus (BIORAD GENE PULSER trade mark). The cells were incubated on ice for a further 15 mins and then plated into 5×96 well plates with 200 μl of medium per well (DMEM, 5% FCS, Pen/Strep, glutamine) or 3×9 cm dishes with 10 mls medium in each dish and incubated overnight. After 24 hrs the medium was removed and replaced with selective media containing xanthine (250 μg/ml), mycophenolic acid (5 μg/ml) and 1× hypoxanthine-thymidine (HT). The cells were fed every third-day. After about 14 days gpt resistant colonies are evident in some of the wells and on the plates. The plates were screened for plasminogen by removing an aliquot of medium from each well or plate and assayed using an ELISA assay. Clones producing plasminogen were scaled up and the expression level monitored to allow the selection of the best producer.

10. ELISA for Human Plasminogen

ELISA plates (Pro-Bind, Falcon) are coated with 50 μl/well of goat anti-human plasminogen serum (Sigma) diluted 1:1000 in coating buffer (4.0 g Na2CO3(10.H2O), 2.93 g NaHCO3 per liter H2O, pH 9.6) and incubated overnight at 4° C. Coating solution is then removed and plates are blocked by incubating with 50 μl/well of PBS/ 0.1% casein at room temperature for 15 minutes. Plates are then washed 3 times with PBS/0.05% Tween 20. Samples of plasminogen or standards diluted in PBS/Tween are added to the plate and incubated at room temperature for 2 hours. The plates are then washed 3 times with PBS/Tween and then 50 μl/well of a 1:1000 dilution in PBS/Tween of a monoclonal antihuman plasminogen antibody (eg #3641 and #36.42 from American Diagnostica, New York, USA) is added and incubated at room temperature for 1 hour. The plates are again washed 3 times with PBS/Tween and then 50 μl/well of horse radish peroxidase conjugated goat anti-mouse IgG (Sigma) is added and incubated at room temperature for 1 hour. Alternatively, the bound plasminogen is revealed by incubation with 50 μl/well of horse radish peroxidase conjugated sheep anti-human plasminogen (The Binding Site). The plates are washed 5 times with PBS/Tween and then incubated with 100 μl/well of peroxidase substrate (0.1M sodium acetate/ citric acid buffer pH 6.0 containing 100 mg/liter 3,3',5,5'-tetramethyl benzidine and 13 mM H2O2. The reaction is stopped after approximately 5 minutes by the addition of 25 μl/well of 2.5M sulphuric acid and the absorbance at 450 nm read on a platereader.

11. Purification of Plasminogen Variants

Plasminogen variants are purified in a single step by chromatography on lysine SEPHAROSE 4B (Pharmacia). A column is equilibrated with at least 10 column volumes of 0.05M sodium phosphate buffer pH 7.5. The column is loaded with conditioned medium at a ratio of 1 ml resin per 0.6 mg of plasminogen variant as determined by ELISA using human glu-plasminogen as standard. Typically 400 ml of conditioned medium containing plasminogen are applied to a 10 ml column (H:D=4) at a linear flow rate of 56 ml/cm/h at 4° C. After loading is complete, the column is washed with a minimum of 5 column volumes of 0.05M phosphate buffer pH 7.5 containing 0.5M NaCl until non-specifically bound protein ceases to be eluted. Desorption of bound plasminogen is achieved by the application of 0.2M epsilon-amino-caproic acid in de-ionised water pH 7.0. Elution requires 2 column volumes and is carried out at a linear flow rate of 17 ml/cm/h. Following analysis by SDS PAGE to check purity, epsilon-amino-caproic acid is subsequently removed and replaced with a suitable buffer, eg Tris, PBS, HEPES or acetate, by chromatography on pre-packed, disposable, PD10 columns containing SEPHADEX G-25M (Pharmacia). (The word SEPHADEX is a trade mark.) Typically, 2.5 ml of each plasminogen mutant at a concentration of 0.3 mg/ml are processed in accordance with the manufacturers' instructions. Fractions containing plasminogen, as determined by A280 are then pooled.

We claim:

1. A plasmin or a precursor thereof, which has been modified so as to exhibit resistance to inhibitors of plasmin, characterised in that the modification comprises the mutation of one or more residues in a region or regions corresponding to residues 17–20, 44–54, 62, 154, 158, and 198–213 (using the numbering of SEQ ID No 2).

2. A plasmin precursor modified so as to exhibit resistance to inhibitors of plasmin, characterized in that the modification comprises one or more of the following mutations: Ser-17 to Leu, Glu-45 to Lys or Arg, or Glu-62 to Lys or Ala, according to the numbering of SEQ ID NO 2.

3. A plasmin precursor modified so as to exhibit resistance to inhibitors of plasmin characterized in that the modification comprises the substitution mutation: Glu-45 to Lys, according to the numbering of SEQ ID NO 2.

4. A plasmin precursor modified so as to exhibit resistance to inhibitors of plasmin characterized in that the modification comprises the substitution mutation: Glu-62 to Lys, according to the numbering of SEQ ID NO 2.

5. A plasmin precursor modified so as to exhibit resistance to inhibitors of plasmin characterized in that the modifications comprise the substitution mutations: Glu-45 to Lys and Glu-62 to Lys, according to the numbering of SEQ ID NO 2.

6. An isolated nucleotide sequence coding for said plasmin precursor of any of claims 2 to 5.

7. A pharmaceutical composition comprising a modified plasmin precursor as claimed in any one of claims 2 to 5, together with a pharmaceutically acceptable carrier.

* * * * *